US012577553B2

(12) United States Patent
He et al.

(10) Patent No.: US 12,577,553 B2
(45) Date of Patent: Mar. 17, 2026

(54) SYSTEM FOR INDUCING MUTATION BASED ON OPTIMIZED ACTIVATION-INDUCED CYTIDINE DEAMINASE

(71) Applicant: Sun Yat-sen University, Guangzhou (CN)

(72) Inventors: Xionglei He, Guangzhou (CN); Li Liu, Guangzhou (CN); Chang Ye, Guangzhou (CN); Kehui Liu, Guangzhou (CN); Shanjun Deng, Guangzhou (CN)

(73) Assignee: Sun Yat-sen University, Guangzhou (CN)

(*) Notice: Subject to any disclaimer, the term of this patent is extended or adjusted under 35 U.S.C. 154(b) by 0 days.

(21) Appl. No.: 19/205,994

(22) Filed: May 12, 2025

(65) Prior Publication Data

US 2025/0270534 A1 Aug. 28, 2025

Related U.S. Application Data

(63) Continuation of application No. 17/489,778, filed on Sep. 30, 2021, now abandoned, which is a
(Continued)

(30) Foreign Application Priority Data

Apr. 13, 2020 (CN) .......................... 202010285948.1

(51) Int. Cl.
| | |
|---|---|
| *C12N 9/78* | (2006.01) |
| *C12N 15/10* | (2006.01) |
| *C12N 15/62* | (2006.01) |

(52) U.S. Cl.
CPC ............. *C12N 9/78* (2013.01); *C12N 15/102* (2013.01); *C12N 15/1024* (2013.01);
(Continued)

(58) Field of Classification Search
CPC .... C12N 9/78; C12N 15/102; C12N 15/1024; C12N 15/62; C07K 2319/09; C07K 2319/80; C12Y 305/04005
See application file for complete search history.

(56) References Cited

U.S. PATENT DOCUMENTS

| | | | | |
|---|---|---|---|---|
| 9,683,226 | B2 * | 6/2017 | Wang | ..................... C07K 16/00 |
| 2020/0172931 | A1 * | 6/2020 | Liu | ........................... C12N 9/22 |

FOREIGN PATENT DOCUMENTS

| | | |
|---|---|---|
| CN | 102482639 A | 5/2012 |
| CN | 103620027 A | 3/2014 |

(Continued)

OTHER PUBLICATIONS

Liu, Kehui, et al. "Mapping single-cell-resolution cell phylogeny reveals cell population dynamics during organ development." Nature Methods 18.12 (Dec. 2021): 1506-1514 (Year: 2021).*
(Continued)

*Primary Examiner* — Terry A McKelvey
*Assistant Examiner* — Andrew T Moehlman

(57) ABSTRACT

The present application provides a mutant protein of activation-induced cytidine deaminase, wherein the mutant protein has the following mutations when compared to hsAID: T82I, K10E, K34E, E156G, 181*, S38C, H130R, V152A, R174G, and T110A. The present application also provides a high-efficiency base editor, including the mutant protein of activation-induced cytidine deaminase of the present application and a DNA-specific binding protein, which are linked sequentially via a linking sequence. The present application also provides a targeted single-base editing system, including a targeted single-base editing protein and a target hyper mutation fragment. Compared with the existing single-base editing system based on activation-induced cytidine deaminase (AID), the system for inducing the mutant protein of
(Continued)

the present application has a smaller molecular weight and higher mutation efficiency.

3 Claims, 16 Drawing Sheets

Specification includes a Sequence Listing.

Related U.S. Application Data continuation-in-part of application No. PCT/CN2020/139973, filed on Dec. 28, 2020.

(52) U.S. Cl.
CPC ...... *C07K 2319/09* (2013.01); *C07K 2319/80* (2013.01); *C12N 15/62* (2013.01); *C12Y 305/04005* (2013.01)

(56) References Cited

FOREIGN PATENT DOCUMENTS

| | | | |
|---|---|---|---|
| CN | 107522787 | A | 12/2017 |
| CN | 109957569 | A | 7/2019 |
| CN | 110914426 | A | 3/2020 |
| WO | 2020051562 | A2 | 3/2020 |

OTHER PUBLICATIONS

Tanaka et al. Attracting Aid to targets of somatic hypermutation. J Exp Med Feb. 15, 2010; 207 (2): 405-415. doi: https://doi.org/10.1084/jem.20090821 (Year: 2010).*

*Homo sapiens* activation induced cytidine deaminase (AICDA), transcript variant 1, mRNA, NCBI Reference Sequence: NM_020661.4, Sequence data retrieved from Genbank, Nov. 22, 2018, available at URL: https://www.ncbi.nlm.nih.gov/nuccore/1519243411?sat=47&satkey=731880.

Shaun M. Lippow et al., Creation of a type IIS restriction endonuclease with a long recognition sequence, Nucleic Acids Research, Mar. 20, 2009, pp. 3061-3073, vol. 37, No. 9.

Notice of Allowance of counterpart Chinese Patent Application No. 202010285948.1 issued on Mar. 26, 2023.

First Office Action of counterpart Chinese Patent Application No. 202010285948.1 issued on Jan. 9, 2023.

* cited by examiner

SEQUENCE LISTING

Sequence total quantity: 14
SEQ ID NO: 1              moltype = DNA  length = 630
FEATURE                   Location/Qualifiers
misc_feature              1..630
                          note = Synthetic
source                    1..630
                          mol_type = other DNA
                          organism = synthetic construct
SEQUENCE: 1
aagcttatgc ccaagaaaaa gcgcaaggtg gacagcctct tgatgaaccg gaggaagttt   60
ctttaccaat tcaaaaatgt ccgctgggct aagggtcggc gtgagaccta cctgtgctac   120
gtagtgaaga ggcgtgacag tgctacatcc ttttcactgg actttggtta tcttcgcaat   180
aagaacggct gccacgtgga attgctcttc ctccgctaca tctcggactg ggacctagac   240
cctggccgct gctaccgcgt cacctggttc acctcctgga gccctgctgcta cgactgtgcc   300
cgacatgtgg ccgactttct gcgagggaac cccaacctca gtctgaggat cttcaccgcg   360
cgcctctact tctgtgagga ccgcaaggct gagcccgagg ggctgcggcg gctgcaccgc   420
gccggggtgc aaatagccat catgaccttc aaagattatt tttactgctg gaatactttt   480
gtagaaaacc acgaaagaac tttcaaagcc tgggaagggc tgcatgaaaa ttcagttcgt   540
ctctccagac agcttcggcg catccttttg cccctgtatg aggttgatga cttacgagac   600
gcatttcgta ctttgggact ttaatctaga                                    630

SEQ ID NO: 2              moltype = DNA  length = 717
FEATURE                   Location/Qualifiers
misc_feature              1..717
                          note = Synthetic
source                    1..717
                          mol_type = other DNA
                          organism = synthetic construct
SEQUENCE: 2
ggatccaaaa acatcaaaaa aaaccaggta atgaacctgg gtccgaactc taaactgctg   60
aaagaataca atcccagct gatcgaactg aacatcgaac agttcgaagc aggtatcggt   120

-continued

```
ctgatcctgg gtaatgctta catccgttct cgtgatgaag gtaaaaccta ctgtatgcag   180
ttcgagtgga aaaacaaagc atacatggac cacgtatgtc tgctgtacga tcagtgggta   240
ctgtccccgc cgcacaaaaa agaacgtgtt aaccacctgg gtaacctggt aatcacctgg   300
ggcgcccaga ctttcaaaca ccaagctttc aacaaactgg ctaacctgtt catcgttaac   360
aacaaaaaaa ccatcccgaa caacctggtt gaaaactacc tgaccccgat gtctctggca   420
tactggttca tggatgctgg tggtaaatgg gattacaaca aaaactctac caacaaatcg   480
atcgtactga acacccagtc tttcactttc gaagaagtag aatacctggt taagggtctg   540
cgtaacaaat tccaactgaa ctgttacgta aaaatcaaca aaaacaaacc gatcatctac   600
atcgattcta tgtcttacct gatcttctac aacctgatca aaccgtacct gatcccgcag   660
atgatgtaca aactgccgaa cactatctcc tccgaaactt tcctgaaatg agaattc     717

SEQ ID NO: 3          moltype = DNA  length = 1293
FEATURE               Location/Qualifiers
misc_feature         1..1293
                      note = Synthetic
source                1..1293
                      mol_type = other DNA
                      organism = synthetic construct
SEQUENCE: 3
atggacagcc tcttgatgaa ccggagggag tttctttacc aattcaaaaa tgtccgctgg    60
gctaagggtc ggcgtgagac ctacctgtgc tacgtagtgg agaggcgtga cagtgctaca   120
tccttttcac tggactttgg ttatcttcgc aataagaacg gctgccacgt ggaattgctc   180
ttcctccgct acatctcgga ctgggaccta gaccctggcc gctgctaccg cgtcacctgg   240
ttcatctcct ggagcccctg ctacgactgt gcccgacatg tggccgactt tctgcgaggg   300
aaccccaacc tcagtctgag gatcttcacc gcgcgcctct acttctgtga ggaccgcaag   360
gctgagcccg aggggctgcg gcggctgcac cgcgccgggg tgcaaatagc catcatgacc   420
ttcaaagatt atttttactg ctggaatact tttgtagaaa accatggaag aactttcaaa   480
gcctgggaag ggctgcatga aaattcagtt cgtctctcca gacagcttcg gcgcatcctt   540
ggtggaggtg gttctggtgg tggaggttct ggtggtggtg gatccatgaa aaacatcaaa   600
aaaaaccagg taatgaacct gggtccgaac tctaaactgc tgaaagaata caaatcccag   660
ctgatcgaac tgaacatcga acagttcgaa gcaggtatcg gtctgatcct gggtaatgct   720
tacatccgtt ctcgtgatga aggtaaaacc tactgtatgc agttcgagtg gaaaaacaaa   780
gcatacatgg accacgtatg tctgctgtac gatcagtggg tactgtcccc gccgcacaaa   840
aagaacgtg ttaaccacct gggtaacctg gtaatcacct ggggcgccca gactttcaaa   900
caccaagctt tcaacaaact ggctaacctg ttcatcgtta acaacaaaaa aaccatcccg   960
aacaacctgg ttgaaaacta cctgaccccg atgtctctgg catactggtt catggatgct  1020
ggtggtaaat gggattacaa caaaaactct accaacaaat cgatcgtact gaacacccag  1080
tctttcactt tcgaagaagt agaatacctg gttaagggtc tgcgtaacaa attccaactg  1140
aactgttacg taaaaatcaa caaaaacaaa ccgatcatct catcgattc tatgtcttac  1200
ctgatcttct acaacctgat caaaccgtac ctgatcccgc agatgatgta caaactgccg  1260
aacactatct cctccgaaac tttcctgaaa taa                                1293

SEQ ID NO: 4          moltype = DNA  length = 1661
FEATURE               Location/Qualifiers
misc_feature         1..1661
                      note = Synthetic
source                1..1661
                      mol_type = other DNA
                      organism = synthetic construct
SEQUENCE: 4
atggacagcc tcttgatgaa ccggagggag tttctttacc aattcaaaaa tgtccgctgg    60
gctaagggtc ggcgtgagac ctacctgtgc tacgtagtgg agaggcgtga ctgtgctaca   120
tccttttcac tggactttgg ttatcttcgc aataagaacg gctgccacgt ggaattgctc   180
ttcctccgct acatctcgga ctgggaccta gaccctggcc gctgctaccg cgtcacctgg   240
ttcatctcct ggagcccctg ctacgactgt gcccgacatg tggccgactt tctgcgaggg   300
aaccccaacc tcagtctgag gatcttcgcc gcgcgcctct acttctgtga ggaccgcaag   360
gctgagcccg aggggctgcg gcggctgcgc cgcgccgggg tgcaaatagc catcatgacc   420
ttcaaagatt atttttactg ctggaatact tttgcagaaa accatggaag aactttcaaa   480
gcctgggaag ggctgcatga aaattcagtt cgtctctccg gacagcttcg gcgcatcctt   540
agcggcagcg agactcccgg gacctcagag tccgccacac cgaaagtaa aaacatcaaa   600
aaaaaccagg taatgaacct gggtccgaac tctaaactgc tgaaagaata caaatcccag   660
ctgatcgaac tgaacatcga acagttcgaa gcaggtatcg gtctgatcct gggtaatgct   720
tacatccgtt ctcgtgatga aggtaaaacc tactgtatgc agttcgagtg gaaaaacaaa   780
gcatacatgg accacgtatg tctgctgtac gatcagtggg tactgtcccc gccgcacaaa   840
aagaacgtg ttaaccacct gggtaacctg gtaatcacct ggggcgccca gactttcaaa   900
caccaagctt tcaacaaact ggctaacctg ttcatcgtta acaacaaaaa aaccatcccg   960
aacaacctgg ttgaaaacta cctgaccccg atgtctctgg catactggtt catggatgtg  1020
gtggtaaatg ggattacaac aaaaactcta ccaacaaatc gatcgtactg aacacccagt  1080
ctttcacttt cgaagaagta gaatacctgg ttaagggtct gcgtaacaaa ttccaactga  1140
actgttacgt aaaaatcaac aaaaacaaac cgatcatcta catcgattct atgtcttacc  1200
tgatcttcta caacctgatc aaaccgtacc tgatcccgca gatgatgtac aaactgccga  1260
acactatctc ctccgaaact ttcctgaaag tggaggtgt tctggtgga ggtggttct  1320
gtggtggatc tggaggcggt gggtccgag gtggcggttc gggcggaggt ggatccacta  1380
acctgtccga catcatcgag aaggagactg gcaagcagct ggtgatccag gagtctattc  1440
tgatgctgcc agaggaggtg aagaggtga tcggcaacaa gccagagtct gatatcctgg  1500
tgcacactgc ctacgacgag tccactgacg aaaacgtgat gctgctgact ccgatgcc  1560
cagaatacaa gccatgggcc ctggtgatt aggactccaa cggcgagaac aagatcaaga  1620
tgctgtctgg tggttctccc aagaagaaga ggaaagtcta a                       1661
```

```
SEQ ID NO: 5              moltype = DNA   length = 1638
FEATURE                  Location/Qualifiers
misc_feature             1..1638
                         note = Synthetic
source                   1..1638
                         mol_type = other DNA
                         organism = synthetic construct
SEQUENCE: 5
atggacagcc tccttatgaa ccggcgagag ttcttgtatc aatttaaaaa cgttcgatgg    60
gcaaagggac ggcgggagac ttacctttgc tatgttgtgg agcggcgaga ttgcgccacc   120
tctttctctc ttgacttcgg ctatctccga aacaagaatg gatgtcacgt agaacttttg   180
tttcttcggt atataagtga ctgggacctt gatccaggac gatgctaccg cgttacctgg   240
ttcatctcat ggagcccctg ttatgactgc gccaggcatg ttgctgactt tctgagaggg   300
aatccaaacc tctccctccg cattttcgct gctaggctgt attttgtga ggatcggaag   360
gcagaaccag agggtctcag gcgattcgcg cgggctggag tacaaatcgc tattatgaca   420
tttaaggact acttttattg ctggaacact ttcgctgaaa atcatggtag aacctttaaa   480
gcctgggagg ggcttcacga gaactcagtc cgattgtcag gtcaactcag gcgcatactg   540
ggaggaggtg gttccggcgg tggggcagt ggcggaggtg gttctatgaa gaatatcaag   600
aaaaatcagg taatgaattt gggtcctaac agtaagttgc tcaaggaata caagtcccaa   660
ctgattgagc tgaacattga acaattcgaa gccggaattg gcttgatact cggcaatgct   720
tatatcagga gtagagatga agggaaaact tattgcatgc aattcgagtg gaaaaataag   780
gcctatatgg atcacgtgtg tctcctttat gaccaatggg tactgtcact tccacatacag   840
aaagagaggg ttaatcatct tggtaatctc gttatcacat ggggagcaca aactttcaaa   900
catcaggcat ttaacaaatt ggcaaacttg tttattgtga acaataaaaa gactataccc   960
aacaatttgg tcgagaacta tcttacccct atgtctttgg cctactggtt catggacgca  1020
ggcggcaaat gggattacaa caaaaatagt acaaacaaag gtattgtact taacacacag  1080
tcctttacat tcgaagaggt agaatatttg gtcaaaggac ttaggaacaa gtttcaactg  1140
aattgttacg ttaaaataaa taaaaataag cctatcatat acatagactc tatgtcttac  1200
ctgattttct acaacttgat aaagccctac ctcattcccc aaatgatgta taaactccca  1260
aatactattt cttccgagac cttcctgaaa tctggtggt ctggaggatc tggtggttct  1320
actaatctgt cagatattat tgaaaaggag accggtaagc aactggttat ccaggaatcc  1380
atcctcatgc tcccagagga ggtggaagaa gtcattggga caagccgga aagcgatata  1440
ctcgtgcaca ccgcctacga cgagagcacc gacgagaatg tcatgcttct gactagcgac  1500
gcccctgaat acaagccttg ggctctggtc atacaggata gcaacggtga gaacaagatt  1560
aagatgctct ctggtggttc ttacccatac gatgttccat attacgctgc agctcccaag  1620
aagaagagga aagtctaa                                                1638

SEQ ID NO: 6              moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 6
tagggataac agggtaat                                                  18

SEQ ID NO: 7              moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 7
attaccctgt tatccta                                                   18

SEQ ID NO: 8              moltype = AA   length = 7
FEATURE                  Location/Qualifiers
source                   1..7
                         mol_type = protein
                         organism = Betapolyomavirus macacae
REGION                   1..7
                         note = NLS - SV40
SEQUENCE: 8
PKKKRKV                                                               7

SEQ ID NO: 9              moltype = DNA   length = 368
FEATURE                  Location/Qualifiers
misc_feature             1..368
                         note = Synthetic
source                   1..368
                         mol_type = other DNA
                         organism = synthetic construct
SEQUENCE: 9
caggtgggta agcaaactgg ttccaatgct ggcacctagg cttgccagca tgcttaggta    60
ggttggtgcc caggtgagct taggaactag cttgccaact agcctgctgg tacacctgtg   120
cctgctagca tgccggttag tacccaggta agcctaccag ttagctatta ccctgttatc   180
cctatacgta gggataacag ggtaatagct agtaggctta ctaacttact aaccggttta   240
```

```
ctccaatgcc agccagccta ggagtttgcc tactagcttg ctagtaggtt caggtgagct   300
agctaaccag caagttggta taccaaccag ttagtaagca tgctggtaag ccagtaaacc   360
tgctggct                                                            368

SEQ ID NO: 10          moltype = DNA  length = 752
FEATURE                Location/Qualifiers
misc_feature           1..752
                       note = Synthetic
source                 1..752
                       mol_type = other DNA
                       organism = synthetic construct
SEQUENCE: 10
tactccaata ggccaaggca ttggcctaca ggtgggctag caagcaagcc tactcaggtg    60
agctagctta cctactagct ggctaaccag ctagcaaacc agcaggtaag ttcacctggg   120
cataggtact ggtacaggtg taggaaccaa ctggcaggta ggtaggtaat taccctgtta   180
tccctatcag tagggataac agggtaatag caaaccggtt agtttaccta ggtgcccacc   240
tgagcaccta agctcaggtg agccggctag ctagctggtt taccttggag cttgcctact   300
caggtgagcc tgccaaccta ctagccagtt ggtttgccgg taggttaacc agttggcaag   360
cctgcccacc tgcaggtgca attccaggtg ggtaagcaaa ctggttccaa tgctggcacc   420
taggcttgcc agcatgctta ggtaggttgg tgcccaggtg agcttaggaa ctagcttgcc   480
aactagcctg ctggtacacc tgtgcctgct agcatgccgg ttagtaccca ggtaagccta   540
ccagttagct attaccctgt tatccctata cgtagggata acagggtaat agctagtagg   600
cttactaact tactaaccgg tttactccaa tgccagccag cctaggagtt tgcctactag   660
cttgctagta ggttcaggtg agctagctaa ccagcaagtt ggtataccaa ccagttagta   720
agcatgctgg taagccagta aacctgctgg ct                                 752

SEQ ID NO: 11          moltype = DNA  length = 2940
FEATURE                Location/Qualifiers
misc_feature           1..2940
                       note = Synthetic
source                 1..2940
                       mol_type = other DNA
                       organism = synthetic construct
SEQUENCE: 11
agcttactaa ccagccaact agctggctag caggtaaacc tgccagcctg ccggctcagg    60
tgagccagtt agtaggcaag taagctcacc tgtaggggct ttggagcagg tattggagta   120
caggtgtagg ttggagttag ccagtaggtt cacctgatta ccctgttatc cctacaggtg   180
agcaggctag caagtaggtt ccaatgccgg ctggtaagca taccaactcc aaagttcacc   240
tgcaggtgta ggtacctagg cacctgcacc tgggcatagg tgctcctaag ctagcaaacc   300
ggtacctata ctcaggtgag ctagcaagct caggtgtagg gataacaggg taatagctaa   360
cctactagtt ggctaacccc aaccaatact taggagctgg caggctagtt tactagctca   420
ggtgcaggtg agtaagtaca cctgtgccag taagcaccta agccaaccag cccaggtgag   480
ccaacttgct ggcaaaccta ctggtatacc attaccctgt tatccctaag ctggtaagct   540
taccccctata ctcacctgtg ccagcccagg tgagcaagtt ggtatacccca cctgcaggtg   600
agtaggctag taagctagct agtatgctag ctggttagtt tgccggctgg ctccaaaact   660
agttggttgg ctcaggtgtg ccggtttagg gataacaggg taattgctcc tacaggtgag   720
taggcttacc agctcaggtg agcaagcttg ctccaatagg taggttggag catgccagtt   780
agctttggag ctcaggtgag tttgccagta ggtaaactag tatacttgct agctggcaag   840
ccggttagta ggctcctaat taccctgtta tccctaccaa aacctgcccc taagctagta   900
taggagccgg ttagccaacc agtaccaacc taagcacacc tgagctagca aactagtacc   960
tatacttgcc agcaggctag cttaccagta agtaggcaca ggtgtcccc taagccagct  1020
ggcaagctta gggataacag ggtaatggct ggcttgccag caggtttacc aactaaccta  1080
ggaaccaact aacttgctcc aaagcaagca aactcacctg ggcatgcccc taagctagta  1140
aacccaggtg agcaggtagg taagtttacc agccaactta cccaggtgaa ccagttcacc  1200
tgattaccct gttatcccta tgctagcata cttgcttgcc ggcatgcttg ctagtaccaa  1260
aactagctgg ttggcacagg tgggcttgct taggcacctg agcaggcagg ctagtaccta  1320
agccaaccgg caagtaagtt agtaggctcc aaagttcagg tgttggagtt aacttaggga  1380
taacagggta atagtaggta ggttagctgg ttagtaagct tgccttggag cttgctagtt  1440
tgctagttta ccaactaacc ggcaagttaa ctttggcacc tgttggtagg cctaagcttg  1500
ccagcccacc tgaacctgcc caggtgggca cacctgagta tgccttggat taccctgtta  1560
tccctaagca cacctgagca agctagtaca ggtgcacctg caggtgccta cacctgggta  1620
ggctaactca cctgtgcctg cctgctggca cacctgaact ggttggcacc tatgccagct  1680
tgccaaccgg cttaggtagg taccagccgg tatactagct aactaaccta gggataacag  1740
ggtaatcacc tgagtaaacc cctaggtaag tacaggtgta caggtttggt ggttccaacc  1800
taagctttgg ttggtgccgg ctggtttacc ggtatactcc aacacctgag ctggtaccta  1860
ggcttactca cctgcaggtg ggctggtacc tatgccaacc aaccattacc ctgttatccc  1920
tacacctgtt ggagctttgg cacctgagca cacctgggct ggcatgctta ggcacctggg  1980
taggcttagg caggtgagca ggctagctgg taggttagcc ggtacacctg agtttactca  2040
ggtgcctaag ctggtttagg agctggtata ggggcattgg taacagggta  2100
atggctggca ggttaaccaa ctaaccaact cctaagccgg taggctagct agcatacctg  2160
ctagccccaa cacctgtacc agcaggcaag ctggctccta aactagtaca ggtgaacctg  2220
ccggctagct agcttagggg ctagccagta ggttattacc ctgttatccc taagctagcc  2280
tgccagctcc tatgctagtt agcaagctgg taggctggct agcctgccta cttaccggtt  2340
ggtaggtaaa cccacctgag catgccggta tgcctagccg agccaacta  2400
ggtgctggca cctatgccta cttagggata cagggtaat aactggctcc aacacctgta  2460
ctagcaagct tgccagcaag tataggcacc tgagctaact agcttaggaa cccacctggg  2520
cataggaacc agctagttag ctccaaagct aaccccctagg ttggtttgcc agcacacctg  2580
tacttaccca cctgtactat taccctgtta tccctaagtt aactcctaag cccacctgta  2640
ccaaccagta ggcattggag ttggctggta cctaggctgg ctagccagct ggtaagcaag  2700
```

-continued

```
caagtttacc caggtgggct cctacaggtg agctcctaag ctcacctggg taccaaggct  2760
ggcaagcaag cctagggata acagggtaat agctggctag ttggtaggct agcttagggg  2820
ctggctaacc agcaggtaag taagcaccaa agcaggttgg taaaccttgg caggtgagtt  2880
ggctagcttt ggaactagcc agtttaccta ggaactagtt cctaagctag taggttagta  2940

SEQ ID NO: 12          moltype = AA  length = 5
FEATURE                Location/Qualifiers
REGION                 1..5
                       note = Synthetic
source                 1..5
                       mol_type = protein
                       organism = synthetic construct
SEQUENCE: 12
GGGGS                                                                5

SEQ ID NO: 13          moltype = AA  length = 545
FEATURE                Location/Qualifiers
source                 1..545
                       mol_type = protein
                       organism = synthetic construct
REGION                 1..545
                       note = synthetic
SEQUENCE: 13
MDSLLMNRRE FLYQFKNVRW AKGRRETYLC YVVERRDCAT SFSLDFGYLR NKNGCHVELL   60
FLRYISDWDL DPGRCYRVTW FISWSPCYDC ARHVADFLRG NPNLSLRIFA ARLYFCEDRK  120
AEPEGLRRLR RAGVQIAIMT FKDYFYCWNT FAENHGRTFK AWEGLHENSV RLSGQLRRIL  180
GGGGSGGGGS GGGGSMKNIK KNQVMNLGPN SKLLKEYKSQ LIELNIEQFE AGIGLILGNA  240
YIRSRDEGKT YCMQFEWKNK AYMDHVCLLY DQWVLSPPHK KERVNHLGNL VITWGAQTFK  300
HQAFNKLANL FIVNNKKTIP NNLVENYLTP MSLAYWFMDA GGKWDYNKNS TNKSIVLNTQ  360
SFTFEEVEYL VKGLRNKFQL NCYVKINKNK PIIYIDSMSY LIFYNLIKPY LIPQMMYKLP  420
NTISSETFLK SGGSGGSGGS TNLSDIIEKE TGKQLVIQES ILMLPEEVEE VIGNKPESDI  480
LVHTAYDEST DENVMLLTSD APEYKPWALV IQDSNGENKI KMLSGGSYPY DVPDYAAAPK  540
KKRKV                                                              545

SEQ ID NO: 14          moltype = AA  length = 198
FEATURE                Location/Qualifiers
source                 1..198
                       mol_type = protein
                       organism = Homo sapiens
SEQUENCE: 14
MDSLLMNRRK FLYQFKNVRW AKGRRETYLC YVVKRRDSAT SFSLDFGYLR NKNGCHVELL   60
FLRYISDWDL DPGRCYRVTW FTSWSPCYDC ARHVADFLRG NPNLSLRIFT ARLYFCEDRK  120
AEPEGLRRLH RAGVQIAIMT FKDYFYCWNT FVENHERTFK AWEGLHENSV RLSRQLRRIL  180
LPLYEVDDLR DAFRTLGL                                                198
```

SYSTEM FOR INDUCING MUTATION BASED ON OPTIMIZED ACTIVATION-INDUCED CYTIDINE DEAMINASE

CROSS-REFERENCE TO RELATED APPLICATIONS

The present application is a Continuation Application of U.S. patent application Ser. No. 17/489,778 filed on Sep. 30, 2021, which is a Continuation-in-part Application of PCT application No. PCT/CN2020/139973 filed on Dec. 28, 2020, which claims the benefit of Chinese Patent Application No. 202010285948.1 filed on Apr. 13, 2020. The contents of the above-identified applications are hereby incorporated by reference.

REFERENCE TO SEQUENCE LISTING

This application includes a Sequence Listing filed electronically as an XML file named "SL_SCH-25039-US-CON.xml", created on May 12, 2025, with a size of 28,835 bytes. The Sequence Listing is incorporated herein by reference.

TECHNICAL FIELD

The present application belongs to the technical field of gene editing, specifically relates to a system and a method for inducing mutations based on an optimized activation-induced cytidine deaminase.

BACKGROUND

Activation-induced cytosine deaminase (AICDA, or AID) is a type of DNA editing enzyme, who plays an important function in somatic hypermutation (SHM), gene conversion and class switch recombination (CSR) in B lymphocytes, by deaminating the DNA of Ig-variable region (V) and Ig-switch region (S), the diversity of the immune repertoire is greatly increased.

Its working principle is generally as follows: First, the cytosine (C) is replaced with uracil (U), and then in the next round of DNA replication, such uracil (U) is converted to thymine (T). If the intracellular repair mechanism detects the presence of uracil (U) in the DNA, there is a certain probability that it will trigger the removal of bases, resulting in a C→G or C→A mutation. DNA deaminase realizes the conversion of cytosine to thymine through deamination, thus triggers DNA mutation (C→T).

Since the birth of the CRISPR/Cas9 system, high-efficiency gene editing gradually become possible. Cas9 is localized to a specific DNA region under the guidance of a short RNA molecule (guide RNA, gRNA). At the target locus, Cas9 endonuclease induces the breakage of the double strand, and then initially repairs through homology directed repair (HDR) mechanism in the form of insertions and deletions (indels). But the efficiency of precise gene editing mediated by homology directed repair is limited, thus limited the wide application of this technology. Therefore, precise gene editing, such as single-base changes, is still a huge challenge for CRISPR technology.

Later, researchers discovered that the single-base editing system developed by integrating base deaminase (such as cytidine deaminase APOBEC1 and adenosine deaminase TadA variants) with the CRISPR/Cas system can accurately introduce point mutations of C/G-T/A and A/T-G/C without cutting DNA double strand, so achieves efficient and accurate gene editing. This gene editing system is still guided by RNA, but it does not cause double-strand breakage at the target locus. In contrast, cytidine deaminase converts cytosine base into uridine, and then being repaired by an error-prone mechanism, thus leads to various point mutations. Moreover, when the uracil-DNA glycosylase pathway is inhibited, the system can also achieve more specific and desired point mutations, such as C-T or G-A transitions. This progress in gene editing is very important, because two-thirds of human genetic diseases are caused by single-base changes. Theoretically, the single-base editing system can be used for the treatment of hundreds of genetic diseases and has great potential for clinical application.

The single-base editing system CRISPR-Cas9-AID based on B cell-specific activation-induced cytidine deaminase (AID) is one of the most important single-base editing technologies.

The mutation efficiency of the existing AID is not high enough. The single-base editing system based on the CRISPR/Cas9 system and AID has a large molecular weight, and thus is not easy to be transported to the target DNA fragments, and restricts the transgenic application in some species. The CRISPR/Cas9 system has a relatively high "off-target" effect.

SUMMARY

The key technical problem solved by the present application is to provide a system for inducing mutations based on an optimized activation-induced cytidine deaminase (denoted as: AID10), which is named "high-efficiency base editor" (abbreviated as HBE) or "targeted single-base editing system". The system can specifically target DNA and induce DNA mutations with high efficiency. At the same time, the present application also provides a method for the system to perform targeted single-base mutation in mice.

In order to achieve the above objectives, the technical solutions adopted by the present application are as follows:

In the first aspect, the present application provides a mutant protein of activation-induced cytidine deaminase (e.g., AID10). The mutant protein has the following mutations when compared to Homo sapiens AID (hsAID, NCBI NP_065712.1 (SEQ ID NO: 14)): T82I, K10E, K34E, E156G, 181* (181* represents a truncating mutation at the 181st amino acid which removes the C-terminal 18 residues), S38C, H130R, V152A, R174G, and T110A.

Further, compared with the sequence set forth in SEQ ID NO: 1, the corresponding nucleotide sequence of the mutant protein has at least 95% sequence identity, preferably at least 98% or 99% sequence identity, more preferably, has 100% sequence identity. It should be noted that although these varieties of nucleotide sequences are different, the different sites in these nucleotides are located in non-critical positions, which have little or even no effect on the efficiency of the mutant protein in targeting DNA and inducing DNA mutations.

In the second aspect, the present application provides a high-efficiency base editor (denoted as: HBE), including the above-mentioned mutant protein of activation-induced cytidine deaminase, a DNA-specific binding protein, and a nuclear localization signal, wherein the mutant protein of the activation-induced cytidine deaminase and the DNA-specific binding protein are sequentially linked via a linking sequence, and the nuclear localization signal is located at the C-terminus of the high-efficiency base editor.

Further, the DNA specific binding protein is a homing endonuclease.

Further, the homing endonuclease includes iScel, iTevl, iSmaMl, piScel, iPpol, piPful, iHmul, iCrel, iCeul, and iAnil.

Further, the corresponding nucleotide sequence of the DNA-specific binding protein consists of SEQ ID NO: 2.

Further, the HBE also includes a UGI (uracil glycosylase inhibitor) protein domain, which is located after the DNA-specific binding protein and before the nuclear localization signal.

The key elements AID10, d-I-SceI (deactivated I-SceI), UGI, and the nuclear localization signal of SV40 (simian virus 40) in the high-efficiency base editor (HBE) of the present application are linked in series via a linking sequence to form a protein having a function of targeted single-base editing. The linking sequence can be adjusted based on the needs of the expression system or the host cells. In the examples, the present application provides HBE proteins suitable for yeast systems, Drosophila, zebrafishes and mice. The key elements AID10, d-I-SceI, UGI, and SV40 in these HBE proteins are the same, and the difference is the linking sequence. In the yeast system, the linking sequence of AID10 and d-I-SceI is 6×(GGGGS) (SEQ ID NO: 12); in Drosophila, the linking sequence is XTEN, 6×(GGGGS); and in the zebrafish and mouse systems, the linking sequence is 6×(GGGGS), GS-rich-linker, and HA. This proves that the linking sequence can be adjusted according to the expression system. Therefore, in the examples, the present application obtains HBE proteins suitable for yeast systems, Drosophila, zebrafishes and mice, and their corresponding nucleotide sequences include SEQ ID NOs: 3-5, respectively.

In the third aspect, the present application provides a targeted single-base editing system, including the above-mentioned high-efficiency base editor and a target hyper mutation fragment.

Further, the nucleotide sequences of the target hyper mutation fragment (abbreviately as HMF) comprises the nucleotide sequences of SEQ ID NO: 6 and SEQ ID NO: 7.

In a fourth aspect, the present application provides a gene editing method, in particular a targeted single-base mutation method, including employing the above-mentioned targeted single-base editing system.

The beneficial effects of the present application are that compared with the existing single-base editing system based on an activation-induced cytidine deaminase (AID), the system for inducing mutant proteins of the present application has a smaller molecular weight and higher mutation efficiency.

BRIEF DESCRIPTION OF THE DRAWINGS

FIG. 6a shows the mutagenic effect of AID5, and FIG. 6b shows the mutagenic effect of AID10. It can be seen from the figures that the mutagenic rate of AID10 is higher than that of AID5.

FIG. 9a is the sequence map of the targeted single-base editing system (HBE) in yeast, and FIG. 9b is the schematic diagram of the 3D structure of the targeted single-base editing system (HBE) in yeast.

FIG. 11a shows induction expression cassettes of the HBE gene; and FIG. 11b shows stable expression cassettes of the Gal4-VP16 gene.

FIG. 17a shows the relative expression of HBE genes in E14 mice in the whole transcriptome, showing that HBE gene expression is normal. FIG. 17b shows the coverage of RNA-seq in the E14 period on the SLOTH system, indicating that the SLOTH system can work normally during the E14 period. FIG. 17c shows the relative expression of the HBE gene in P1 mice in the whole transcriptome, indicating no significant difference from the E14 period, and showing that HBE can still be expressed normally during this period. FIG. 17d shows the coverage of RNA-seq in the P1 period on the SLOTH system. The dots in FIGS. 17a and 17c indicate the expression levels of different genes; the biggest dot in FIGS. 17a and 17c indicates the expression level of HBE gene respectively; and the darker dots and lighter dots in FIGS. 17a and 17c are marked for distinguishing genes in neighbouring chromosomes.

FIG. 18a shows the number of mutations per unit labeling sequence in mice with uninduced expression (HBE⁻) and mice with induced expression (HBE⁺). FIG. 18b shows the number of mutations per unit labeling sequence in mice with induced expression (HBE⁺) at birth (P0) and one day after birth (P1). FIG. 18c shows the number of mutations in different organs of the mice with induced expression.

DETAILED DESCRIPTION

In order to show the technical solutions, objectives and advantages of the present application more concisely and clearly, the present application will be further described in detail below in combination with specific embodiments and the accompanying drawings.

Example 1 Design and Optimization of Activation-Induced Cytidine Deaminase (AID)

1. Screening AID Having a High Mutation Rate

Figure 1:
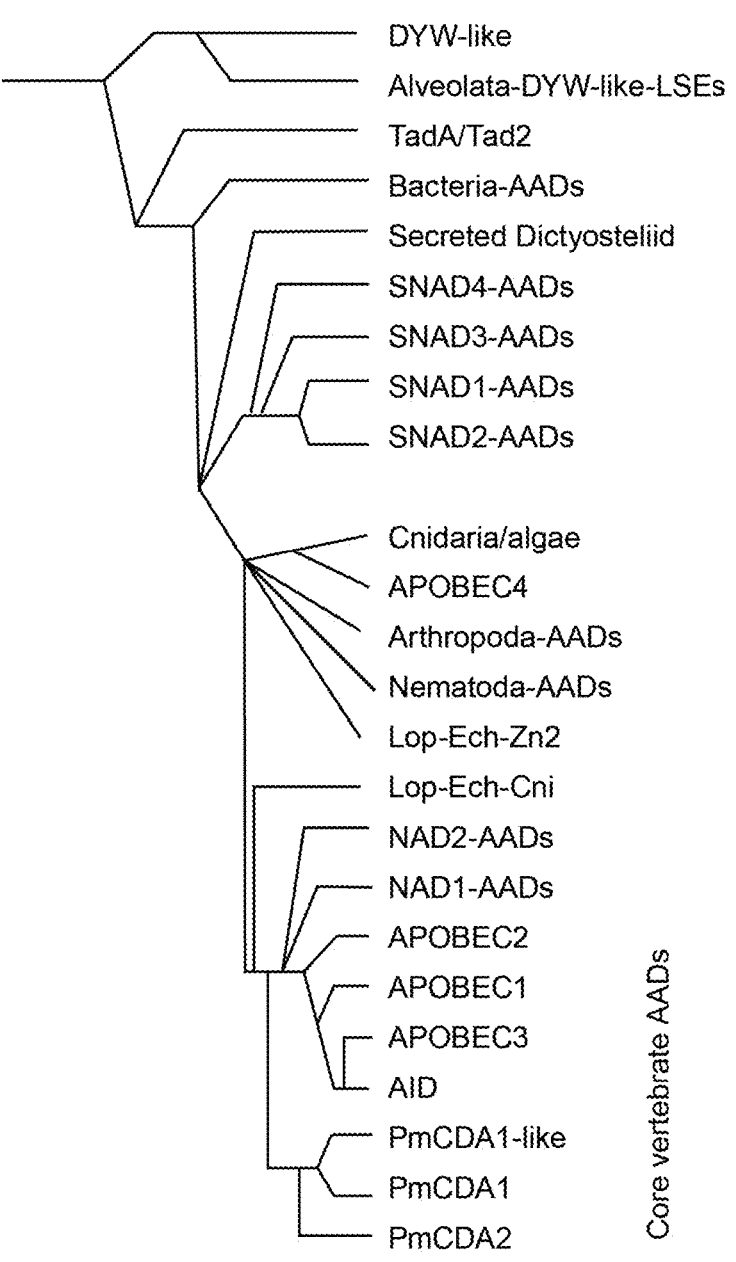
FIG. 1 is a schematic diagram of the evolutionary tree of the deaminase gene family.
Figure 2:
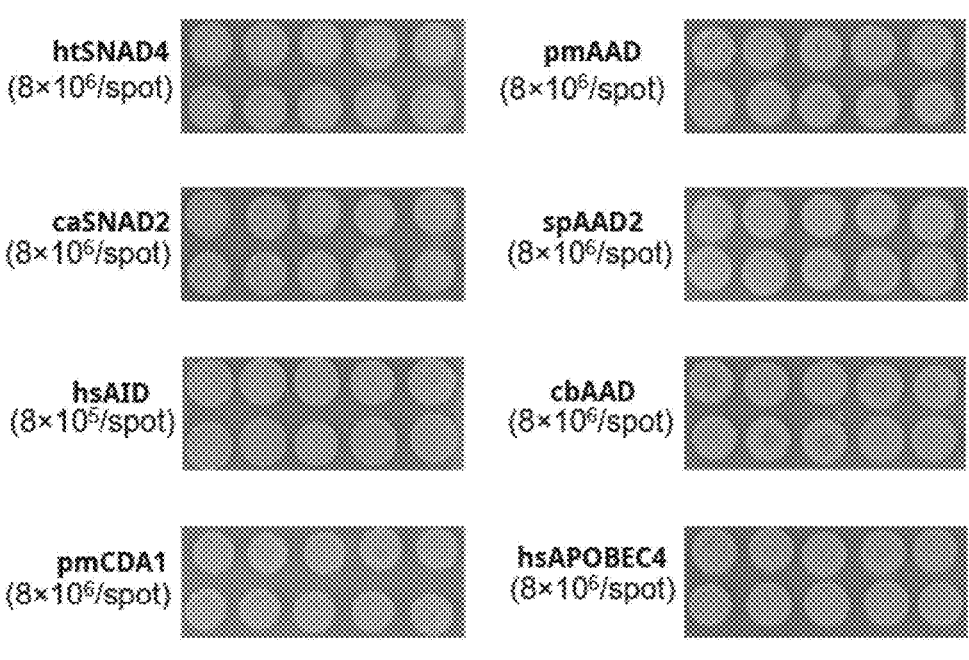
FIG. 2 is a schematic diagram of the results of screening different deaminases through the yeast spot assay.
Figure 3:
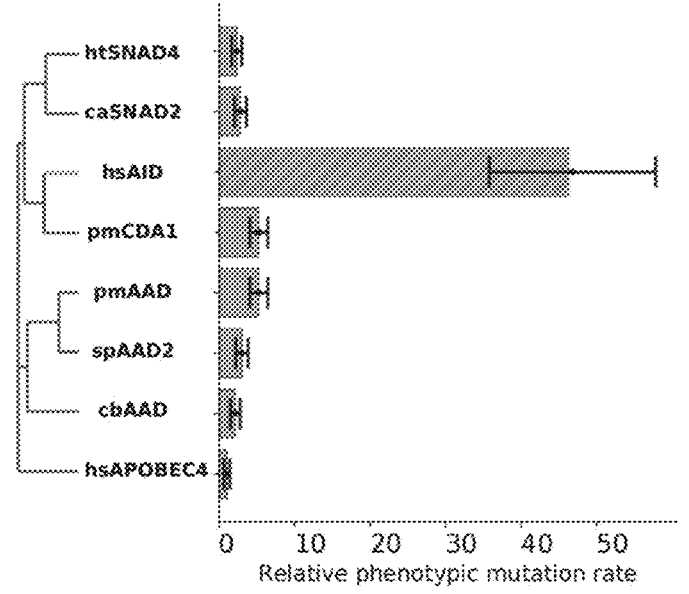
FIG. 3 is a schematic diagram of the comparison results of the mutagenic efficiency of different deaminases (the vertical coordinate represents different deaminases, and the horizontal coordinate represents the mutation rate).

The sequence of the deaminase gene family was obtained through sequence alignment, and classified into several major categories according to its structure on the evolutionary tree (FIG. 1). Moreover, one representative deaminase was selected from each main branch for downstream screening experiments. On the evolutionary tree, there are several deaminases in each main branch, which are derived from different species, thus one deaminase is selected from each branch, and the specific types of representative deaminases selected are the 8 deaminases shown in FIGS. 2 and 3.

The deaminase gene was integrated into the induction expression vector (pGA) after codon optimization, and the mutation efficiency was determined in the yeast platform. The results can be seen in FIG. 2 that GIL104 yeast expressing different deaminases all appeared resistant clones on the SC-Arg–/CAN+ plate, indicating the successful expression of the deaminase gene. In the experiment, each sample had 36 independent replicates of spot plates. The number of yeast cells in each replicate of the spot plate was $8\times10^6$. In addition, due to the large number of clones, the hsAID sample was diluted 10 times before sample spotting, that is $8\times10^5$.

By calculating the number of resistant clones, the mutation efficiency of each deaminase was estimated. From the analysis results (FIG. 3), it can be seen that the hsAID protein has the highest mutation efficiency. HsAID is a human-derived "activation-induced cytosine deaminase" (AICDA, or AID), involved in somatic hypermutation (SHM), gene conversion and B lymphocytes class-switching recombination (CSR). Through the deamination of Ig variable region (V) and Ig switch region(S) DNA, it greatly increases the diversity of the immune repertoire.

Therefore, the subsequent experiments started with hsAID, and thus the AID protein was modified and optimized.

2. Transforming and Optimizing AID to Obtain the Mutator

A semi-rational design strategy was applied. With the help of bioinformatics methods, based on homologous protein sequence alignment, three-dimensional structure or existing knowledge, multiple amino acid residues were selected as targets for modification. In combination with the rational selection of effective codons, and by constructing a high-quality mutant library, substitutions at 6 amino acid positions including K10E, K34E, T82I, F115E, E156G, and R174E were tested. In addition, according to the annotation of the AID protein domain, the C-terminus of the protein mediates the class switch recombination of immune gene loci. Therefore, it is inferred that removing the C-terminus of the AID protein can improve the stability of the target sequence and improve the mutation efficiency.

Figure 4:
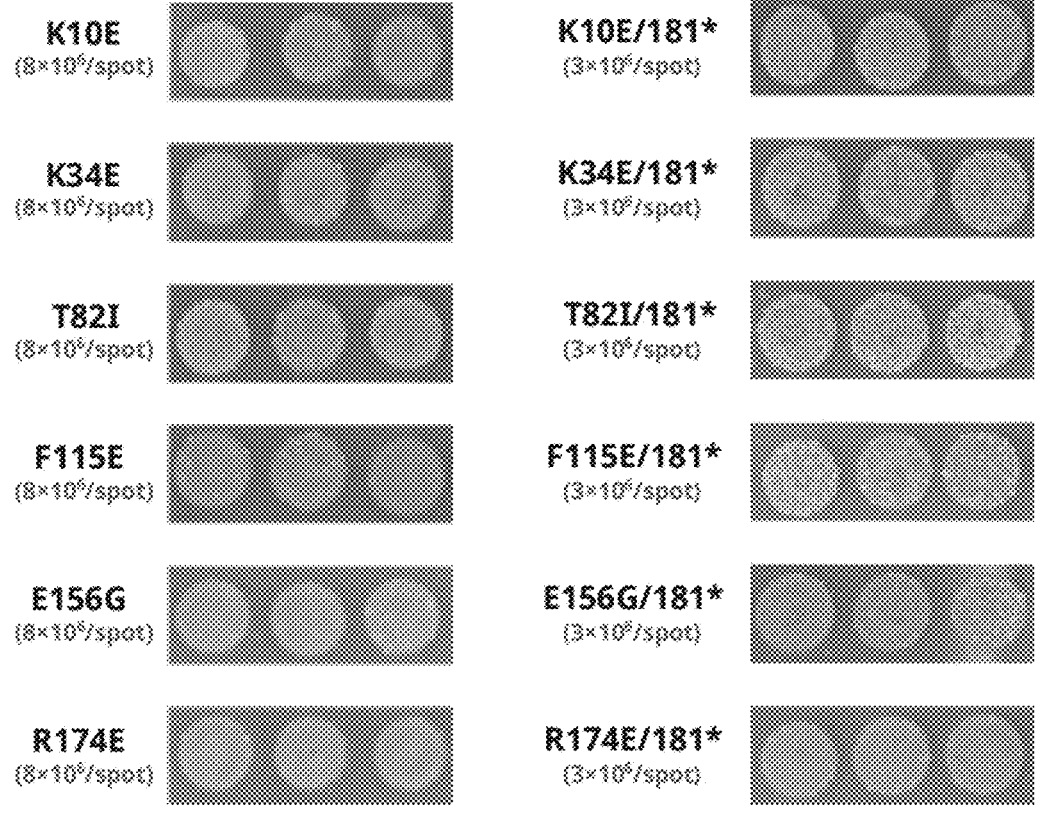
FIG. 4 is a schematic diagram of the results of screening hsAID variants through the yeast spot assay.

The combinations of these loci were tested in the same yeast screening platform to observe whether the efficiency of deaminase mutation can be improved. The test results are shown in FIG. 4. K10E, K34E, T82I, and E156G improve mutation efficiency more obviously, and T82I has the most significantly improved efficiency. At the same time, the 181* variants with early termination also greatly improved the mutation efficiency.

Figure 5:
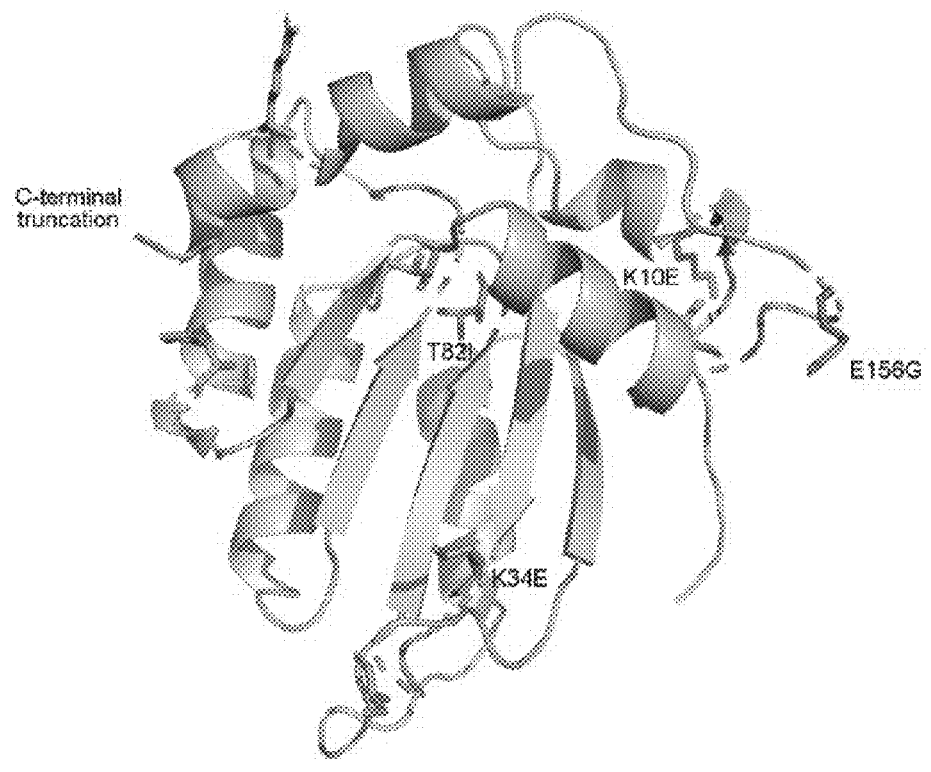
FIG. 5 is a schematic diagram of the protein mutation loci and 3D structure of hsAID mutant AID5.

As shown in FIG. 5, according to the protein 3D structure, the amino acid residues K10E, K34E, E156G, and 181* (not shown) among the five mutation positions are all located on the surface of the protein, while T82I is located inside the protein structure. However, in terms of effect, the improvement brought by the T82I mutation is the most obvious. It may be because the mutation from polar amino acid (Thr) to hydrophobic amino acid (Ile) affects the overall structure of the protein, resulting in an overall improvement in catalytic efficiency. The optimized deaminase protein with improved mutation efficiency was obtained, and it was named AID5. In the following description, "activation-induced cytidine deaminase" (mutator) is referred to as "mutator" for abbreviation.

Example 2 Screening and Optimization of DNA-Specific Binding Proteins

The reason why AID protein can induce high mutations at specific locus in vivo is due to a large number of cofactors and complex time-conditioning control mechanisms. In case of one simple over-expression of AID protein, on the one hand, the mutation rate cannot reach a high level, and on the other hand, mutations will be randomly generated in all positions of the genome, thus triggering mutation burden. Therefore, the job of the "targeted recording" system requires the assistance of DNA-specific binding proteins. The "mutator" is pulled by a DNA-specific binding protein to target specific regions in the genome. In the following description, "DNA specific binding protein" is referred to as "targeter" for abbreviation.

Currently widely used DNA-specific binding proteins can be classified into three categories: zinc finger proteins, TALEN™ proteins, and CRISPR/Cas proteins. Among them, zinc finger proteins have short recognition sequences and poor scalability. Generally, its one protein domain only recognizes specific 3 bases (nucleotide triplets), and therefore multiple protein domains need to be linked in series to recognize specific sequences. In a TALEN™ protein, each structural unit specifically recognizes a single base. By the combination of structural units, the recognition of any sequence can be achieved. However, there are a large number of repeating sequences in the DNA encoding TALEN™ proteins, which are prone to develop recombination and thus are not conducive to the construction of stable transgenic lines. CRISPR/Cas is currently the most widely accepted technology. It relies on specific guide RNA (gRNA) to achieve the binding of specific DNA sequences and it is convenient for modification. However, as a targeting protein, there are also several shortcomings: The protein structure is large (~160 kDa), and as a binding protein, it will produce steric resistance effect, thus affects the function of the linking group; the long gene sequence (~4 kb) has restrictions on the transgenic application of some species; and strong protein binding ability reduces the possibility of single-strand opening, resulting in a shortened window for effective mutation of deaminase.

"Homing endonucleases" are meganucleases that recognize DNA sequences of 14-40 bp in length, which are very rare in the genome. By exogenously expressing a homing endonuclease, homology directed repair can be specifically activated. I-SceI is a homing endonuclease found in yeast. Its recognition sequence (5'-TAGGGATAACAGGGTAAT-3', SEQ ID NO: 6) is as long as 18 base pairs (bp) and has extremely high specificity. The peptide chain of the I-SceI protein is 234 amino acids in length, and the space structure is small. The cleavage active site of I-SceI can be mutated (D44N and D145A) to remove the cleavage activity of the protein, while retaining the ability of DNA binding. Therefore, deactivated I-SceI (denoted as: d-I-SceI) can be used as a specific DNA binding protein, and its nucleotide sequence is set forth in SEQ ID NO: 2. Therefore, I-SceI was selected for subsequent experiments.

Example 3 Preparation Of High-Efficiency Base Editor (HBE) (Yeast System)

Through the screening and optimization of "mutator" and "targeter", the two core parts of the "recording protein" in the target recording system were initially obtained. A flexible peptide chain was used to connect the two parts to obtain the prototype of the recording protein. Then, by overall optimizing the fusion protein, and adding other enhancing elements, the "high-efficiency base editor (HBE)" (or targeted single-base editing protein) was obtained.

Further optimizing and screening of the AID protein: Using the AID5 protein in Example 1 as a template, a mutation library of the AID protein was obtained by error-prone PCR. In the final library, each molecule contained about 4 base substitution mutations. After gel recovery, the AID library was constructed into the pGA induction vector with a library size of about $10^5$. The plasmid library was transformed into GIL104 yeast strain by the lithium acetate transformation method, and positive clones were screened on SC-Leu–/GLU+ agar plate. About 3000 yeast single clones were randomly picked and inoculated into SC-Leu–/GAL+ liquid medium to induce the expression of AID protein. Each single clone was independently induced in a 96-well plate, and the pGA-AID5 strain was set as the control group. The spot assay was the same as the above experiment method.

Figure 6A:
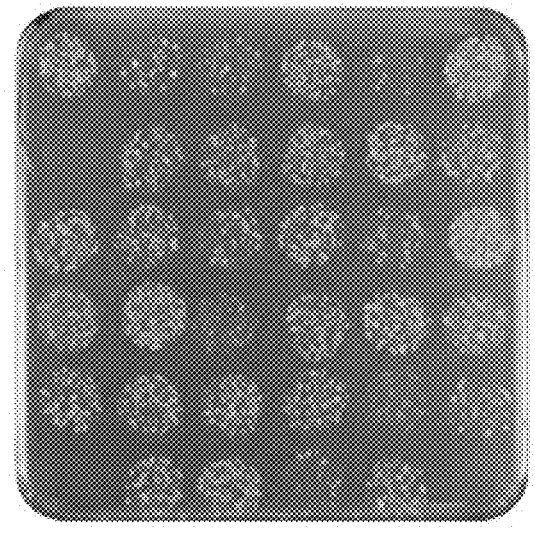
FIGS. 6a-6b are schematic diagrams of comparing the mutagenic efficiency of AID5 and AID10 by the yeast spot assay. Among them.
Figure 6B:
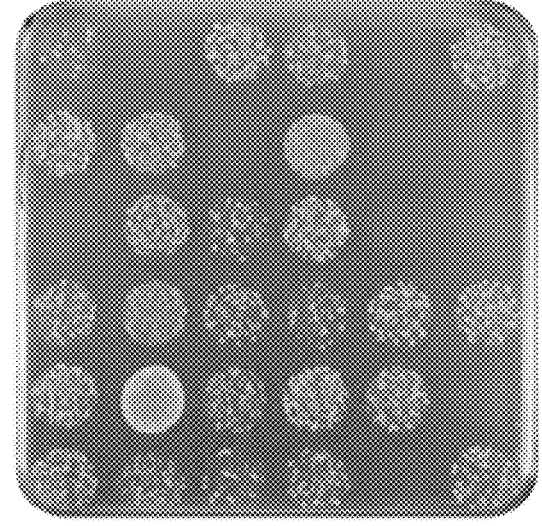
Figure 7:
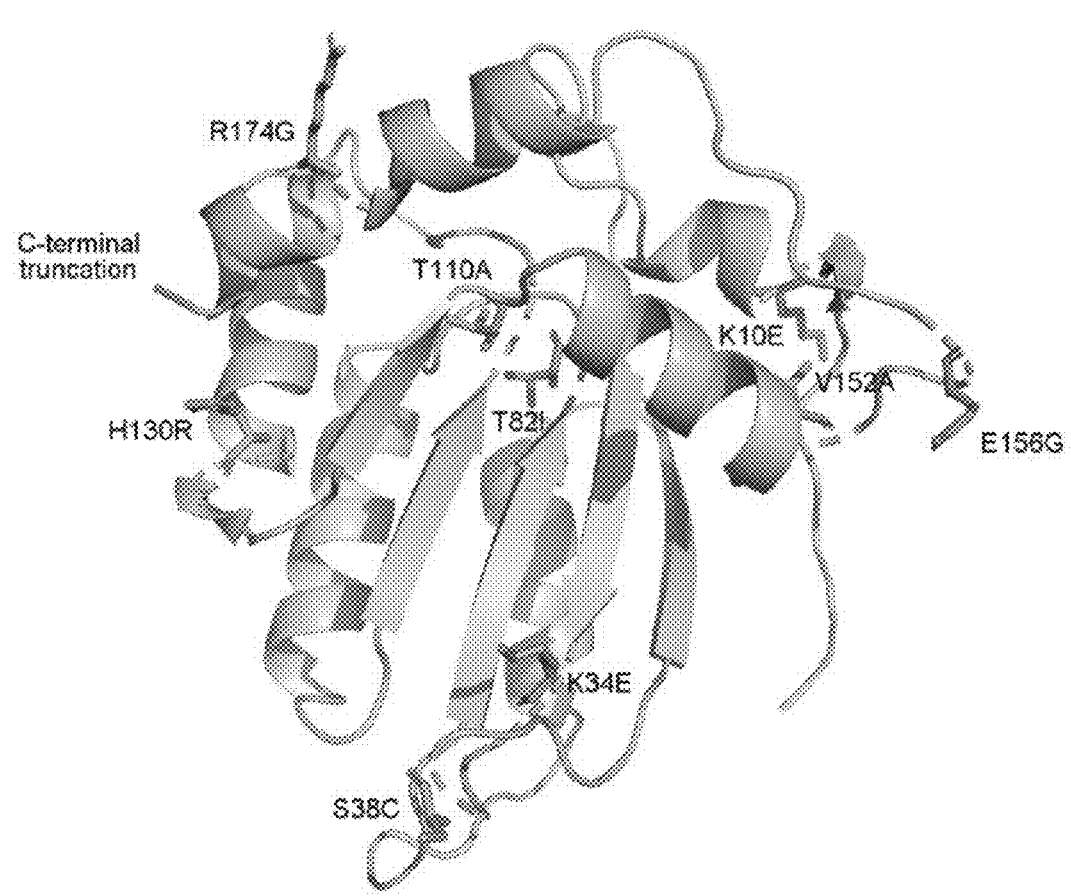
FIG. 7 is a schematic diagram of protein mutation positions and 3D structure of hsAID mutant AID10.

According to the results of the spot assay, the mutants with a higher number of resistant clones than the control group (AID5) were selected, and the sequence of the AID mutant was amplified by yeast colony PCR for Sanger sequencing. Since the library screening method only comes from a single experimental repeating, the estimation of mutation efficiency is affected by the fluctuation effect. Therefore, the amplified gene was reconstituted into the pGA vector for the second round of screening through the spot assay. In the second round of screening, 20 parallel induction experiment groups were set up for each clone. Finally, through the fluctuation analysis of the spot assay results in the second round of screening, a mutant with a slight increase in mutation efficiency (FIG. 6a and FIG. 6b) was found. From the results of Sanger sequencing, another five missense mutations were newly obtained from this variant, plus the original five mutations, in total contained 10 amino acid substitutions (FIG. 7). This variant is named AID10. Further analysis of the spatial location of the mutation position of AID10 shows that S38C, H130R, V152A, and R174G are all located on the surface of the protein, and the residue corresponding to T110A is located inside the 3D structure of the protein. Its nucleotide sequence is set forth in SEQ ID NO: 1.

Further optimization and screening of DNA-specific binding proteins: In order to replace and screen better binding proteins, other proteins in the homing endonuclease family were also inactivated at the cleavage site. After being linked to the AID10 protein, they were also tested for DNA binding capability. The test strain was GIL104 yeast with the corresponding binding sequence integrated downstream of the CAN1 gene. The process of the spot assay and fluctuation analysis was similar to the above.

Figure 8:
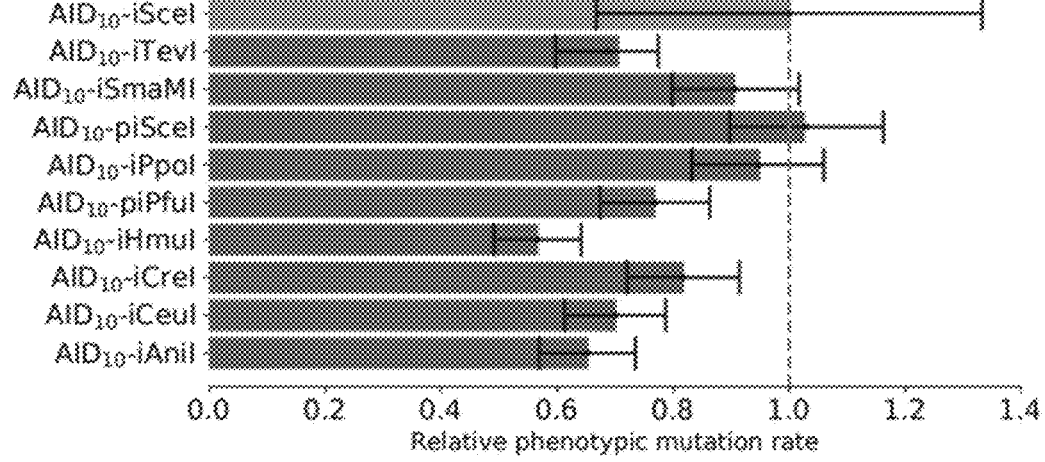
FIG. 8 is a schematic diagram of the screening results of DNA binding proteins (the vertical coordinate indicates different DNA binding proteins, and the horizontal coordinate indicates the mutation rate).

From the results of the fluctuation analysis (FIG. 8), it can be found that using different homing endonucleases as binding domains, all has good mutation efficiency. This means that several binding domains and binding sequences can be orthogonally used in subsequent applications, thereby reducing the repetitiveness of the labeling sequence and increasing the density of mutations. Among them, the I-SceI protein has a slight advantage, therefore I-SceI was used as the binding element in HBE in all subsequent experiments.

The nuclear localization of the protein is the prerequisite for HBE to act on DNA. The N-terminal of the AID protein carries a human-derived nuclear localization signal, but in cross-species applications, the human-derived localization signal may be relatively inferior. Therefore, in downstream applications, the SV40 nuclear localization signal was added to the C-terminus of the HBE protein. The SV40 nuclear localization signal is derived from the large T antigen of the virus SV40 (sequence: PKKKRKV, SEQ ID NO: 8), which had been verified to have a good localization effect in multiple species.

Figure 9A:
FIGS. 9a-9b are the sequence map of the high-efficiency base editor (HBE) in yeast and the schematic diagram of the protein 3D structure. Among them.
Figure 9B:
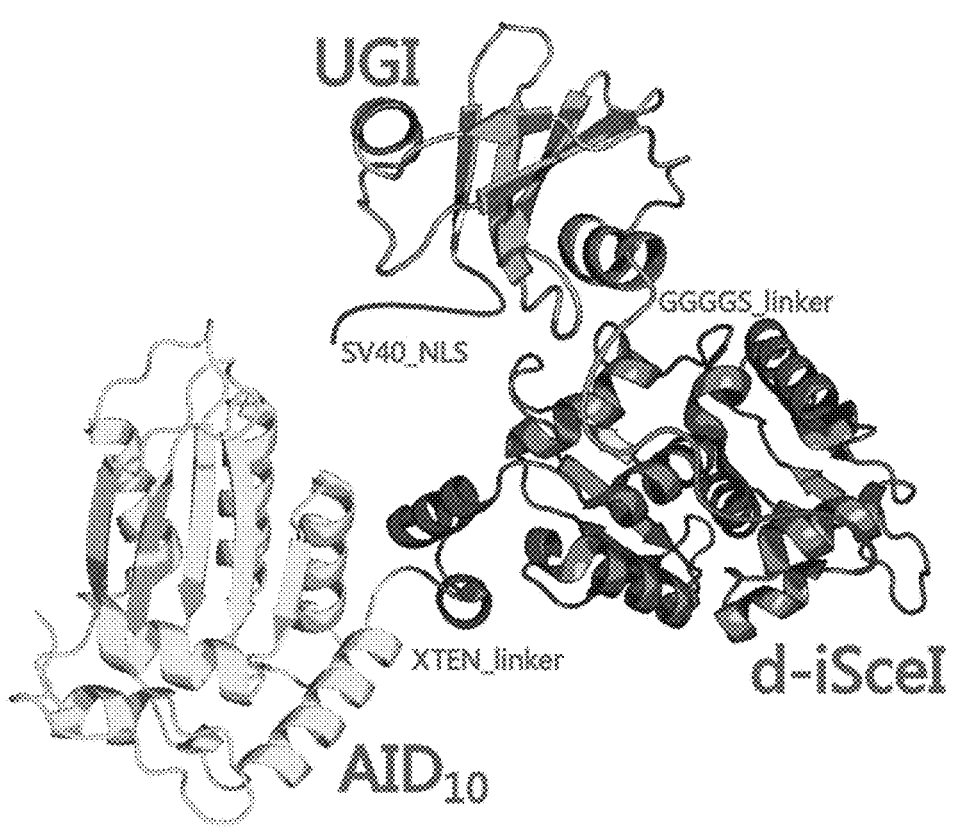

After the cytosine is mutated to uracil, the DNA uracil carboxylase (uracil DNA glycosylase, Ung) in vivo can recognize the abnormalities of the DNA and repair them. Uracil glycosylase inhibitor (UGI) was found in *Bacillus subtilis* bacteriophage PBS2. This protein can form a complex structure with Ung protein, thereby weakening the deamination ability to repair mutations. Therefore, adding the UGI protein domain to the HBE protein improves the efficiency of deaminase mutagenesis. The final HBE protein structure applied to the lineage is shown in FIGS. 9a and 9b. In this example, the HBE protein suitable for the yeast system was finally obtained, and its nucleotide sequence is set forth in SEQ ID NO: 3.

Example 4 Preparation of HBE Protein in *Drosophila*

Figure 10:
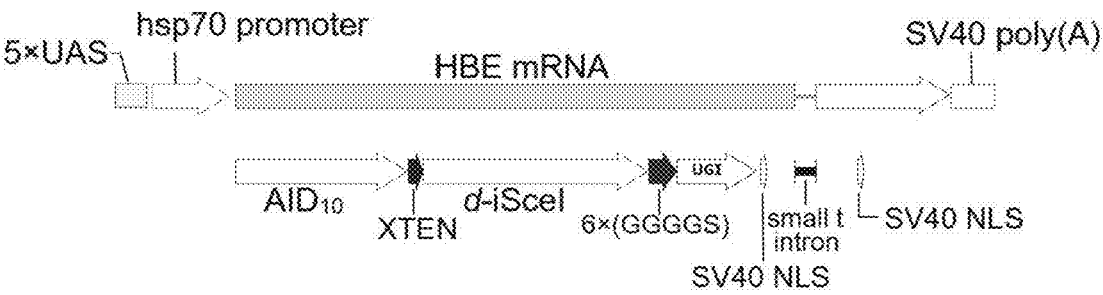
FIG. 10 is a sequence map of the HBE protein in Drosophila.

The HBE protein in *Drosophila* realizes controllable expression in time and space under the control of the GALA-UAS system (FIG. 10). The HBE protein from the N-terminal to C-terminal is hsp70 promoter, AID10, the linking sequence of XTEN protein, d-I-SceI, the protein linker of 6×(GGGGS) (SEQ ID NO: 12), UGI, and the SV40 nuclear localization signal. Gene expression is driven by the upstream UAS sequence (5×GAL4 binding sites) and terminated by the downstream SV40 polyA signal. Its nucleotide sequence is set forth in SEQ ID NO: 4.

Example 5 Preparation of HBE Protein in Zebrafishes and Mice

Figure 11A:
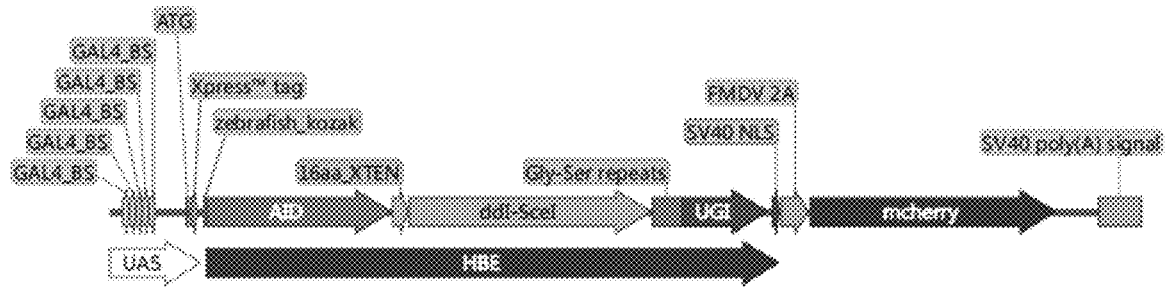
FIGS. 11a-11b are the sequence maps of the HBE protein in zebrafishes and mice. Among them.
Figure 11B:
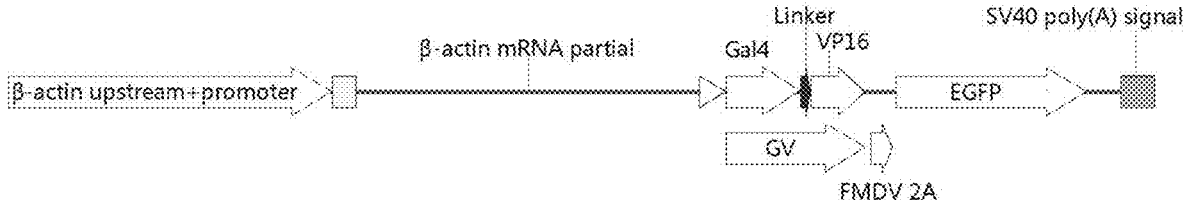

The structure of the zebrafish HBE protein is the same as that in *Drosophila* (FIG. 11a). The zebrafish HBE protein from the N-terminus to C-terminus is AID10, the linker of XTEN protein, d-I-SceI, the protein linker of 6×(GGGGS) (SEQ ID NO: 12), UGI, and the SV40 nuclear localization signal, respectively. The HBE protein is linked to mCherry protein through a self-cleavable foot-and-mouth disease virus (FMDV) 2A peptide. HBE and mCherry were co-transcribed and translated, and the two were cleaved after the protein matures. Therefore, the brightness of mCherry can be used to characterize the concentration of HBE protein. Gene expression was driven by the upstream UAS sequence (5×GAL4 binding sites) and terminated by the downstream SV40 polyA signal. Gal4-VP16 protein (FIG. 11b) can specifically bind to UAS sequence and induce gene expression. Similarly, Gal4-VP16 protein is linked to EGFP through FMDV 2A, and the brightness of EGFP represents the expression level of Gal4-VP16. The nucleotide sequence encoding the HBE protein (or targeted single-base editing protein) is set forth in SEQ ID NO: 5. The amino acid sequence of the HBE protein is set forth in SEQ ID NO: 13.

Example 6 Design and Optimization of the Target Hyper Mutation Fragment (HMF)

Through manual design and optimization, after obtaining the targeted recording protein (HBE), the problem of targeting fragment also needs to be solved. On the one hand, since the I-SceI recognition sequence is fixed, the recognized sequence does not exist in the genome of higher model organisms, and thus it is necessary to introduce an exogenous targeting fragment. However, the length of the exogenous targeting fragment is bound to be limited. On the other hand, because deaminase-induced mutations are sequence-biased, it is necessary to design target mutation hotspots.

Figure 12:
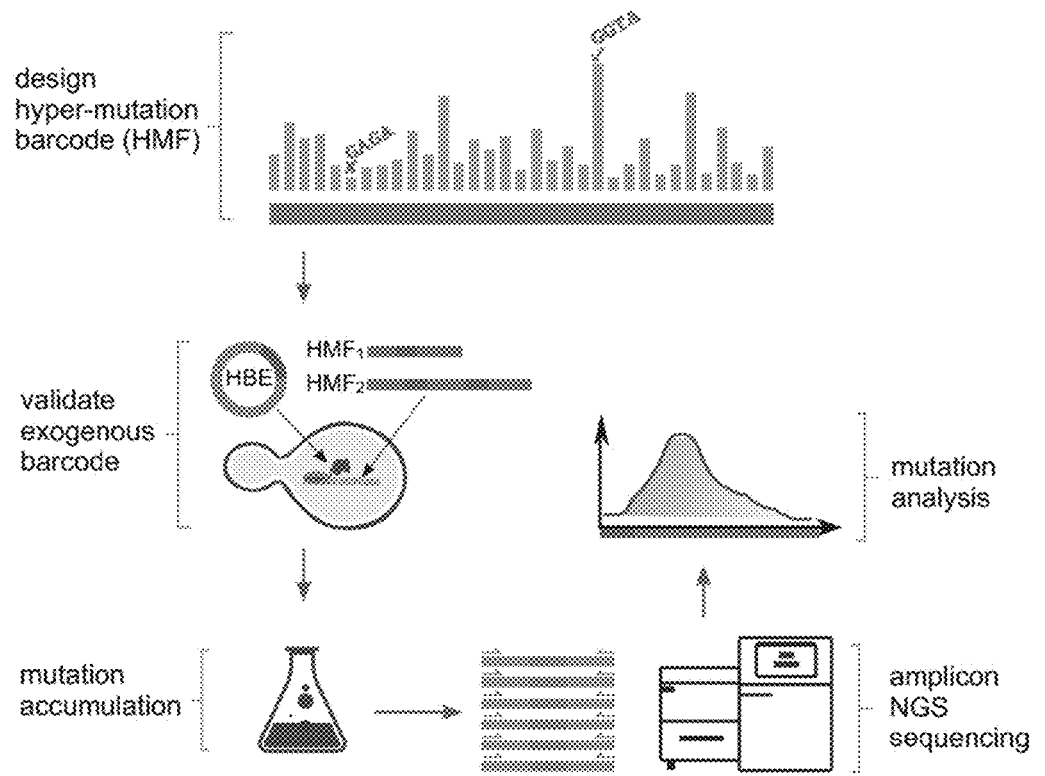
FIG. 12 is a flow chart of the design and optimization of the target hyper mutation fragment (HMF).

Therefore, in this embodiment, the target fragment suitable for higher model organisms was designed, and the design and optimization process are shown in FIG. 12, including three steps:

1) According to the known mutation loci, training the scoring algorithm, designing and screening out the "target hyper mutation fragments" (abbreviated as HMF). (in silico)
2) Introducing the sequence into the system expressing HBE protein, and analyzing the mutation rate of the target fragments through high-throughput sequencing data. (yeast)
3) Designing the target fragment according to the analysis result. (in silico)

The final target hyper mutation fragments are as follows:

```
Forward I-SceI binding motif:
                                    (SEQ ID NO: 6)
5'-TAGGGATAACAGGGTAAT-3';

Reverse I-SceI binding motif:
                                    (SEQ ID NO: 7)
5'-ATTACCCTGTTATCCCTA-3'.
```

The above target hyper mutation fragments were used in yeast to test the targeting ability, and the results are as follows:

```
>HMF1 (368 bp)
                                    (SEQ ID NO: 9)
CAGGTGGGTAAGCAAACTGGTTCCAATGCTGGCACCTAGGCTTGCCAGCA

TGCTTAGGTAGGTTGGTGCCCAGGTGAGCTTAGGAACTAGCTTGCCAACT

AGCCTGCTGGTACACCTGTGCCTGCTAGCATGCCGGTTAGTACCCAGGTA

AGCCTACCAGTTAGCTATTACCCTGTTATCCCTATACGTAGGGATAACAG

GGTAATAGCTAGTAGGCTTACTAACTTACTAACCGGTTTACTCCAATGCC

AGCCAGCCTAGGAGTTTGCCTACTAGCTTGCTAGTAGGTTCAGGTGAGCT

AGCTAACCAGCAAGTTGGTATACCAACCAGTTAGTAAGCATGCTGGTAAG

CCAGTAAACCTGCTGGCT

>HMF2 (752 bp)
                                    (SEQ ID NO: 10)
TACTCCAATAGGCCAAGGCATTGGCCTACAGGTGGGCTAGCAAGCAAGCC

TACTCAGGTGAGCTAGCTTACCTACTAGCTGGCTAACCAGCTAGCAAACC

AGCAGGTAAGTTCACCTGGGCATAGGTACTGGTACAGGTGTAGGAACCAA

CTGGCAGGTAGGTAGGTAATTACCCTGTTATCCCTATCAGTAGGGATAAC

AGGGTAATAGCAAACCGGTTAGTTTACCTAGGTGCCCACCTGAGCACCTA

AGCTCAGGTGAGCCGGCTAGCTAGCTGGTTTACCTTGGAGCTTGCCTACT

CAGGTGAGCCTGCCAACCTACTAGCCAGTTGGTTTGCCGGTAGGTTAACC

AGTTGGCAAGCCTGCCCACCTGCAGGTGCAATTCCAGGTGGGTAAGCAAA

CTGGTTCCAATGCTGGCACCTAGGCTTGCCAGCATGCTTAGGTAGGTTGG

TGCCCAGGTGAGCTTAGGAACTAGCTTGCCAACTAGCCTGCTGGTACACC

TGTGCCTGCTAGCATGCCGGTTAGTACCCAGGTAAGCCTACCAGTTAGCT

ATTACCCTGTTATCCCTATACGTAGGGATAACAGGGTAATAGCTAGTAGG

CTTACTAACTTACTAACCGGTTTACTCCAATGCCAGCCAGCCTAGGAGTT

TGCCTACTAGCTTGCTAGTAGGTTCAGGTGAGCTAGCTAACCAGCAAGTT

GGTATACCAACCAGTTAGTAAGCATGCTGGTAAGCCAGTAAACCTGCTGG

CT
```

The above target hyper mutation fragments were used in Drosophila, zebrafishes, or mice to test the targeting ability, and the results are as follows:

```
>HMF3k (2940 bp)
                                    (SEQ ID NO: 11)
AGCTTACTAACCAGCCAACTAGCTGGCTAGCAGGTAAACCTGCCAGCCTGC

CGGCTCAGGTGAGCCAGTTAGTAGGCAAGTAAGCTCACCTGTAGGGGCTTTGGAGC

AGGTATTGGAGTACAGGTGTAGGTGGAGTTAGCCAGTAGGTTCACCTGATTACCC

TGTTATCCCTACAGGTGAGCAGGCTAGCAAGTAGGTTCCAATGCCGGCTGGTAAGC

ATACCAACTCCAAAGTTCACCTGCAGGTGTAGGTACCTAGGCACCTGCACCTGGGCA

TAGGTGCTCCTAAGCTAGCAAACCGGTACCTATACTCAGGTGAGCTAGCAAGCTCAG

GTGTAGGGATAACAGGGTAATAGCTAACCTACTAGTTGGCTAACCCCAACCAATA

CTTAGGAGCTGGCAGGCTAGTTTACTAGCTCAGGTGCAGGTGAGTAAGTACACCTGT

GCCAGTAAGCACCTAAGCCAACCAGCCCAGGTGAGCCAACTTGCTGGCAAACCTAC

TGGTATACCATTACCCTGTTATCCCTAAGCTGGTAAGCTTACCCCTATACTCACCTG

TGCCAGCCCAGGTGAGCAAGTTGGTATACCCACCTGCAGGTGAGTAGGCTAGTAAG
```

-continued

```
CTAGCTAGTATGCTAGCTGGTTAGTTTGCCGGCTGGCTCCAAAACTAGTTGGTTGGC

TCAGGTGTGCCGGTTTAGGGATAACAGGGTAATTGCTCCTACAGGTGAGTAGGCTT

ACCAGCTCAGGTGAGCAAGCTTGCTCCAATAGGTAGGTTGGAGCATGCCAGTTAGCT

TTGGAGCTCAGGTGAGTTTGCCAGTAGGTAAACTAGTATACTTGCTAGCTGGCAAGC

CGGTTAGTAGGCTCCTAATTACCCTGTTATCCCTACCAAAACCTGCCCCTAAGCTA

GTATAGGAGCCGGTTAGCCAACCAGTACCAACCTAAGCACACCTGAGCTAGCAAAC

TAGTACCTATACTTGCCAGCAGGCTAGCTTACCAGTAAGTAGGCACAGGTGTGCCCC

TAAGCCAGCTGGCAAGCTTAGGGATAACAGGGTAATGGCTGGCTTGCCAGCAGGT

TTACCAACTAACCTAGGAACCAACTAACTTGCTCCAAAGCAAGCAAACTCACCTGG

GCATGCCCCTAAGCTAGTAAACCCAGGTGAGCAGGTAGGTAAGTTTACCAGCCAAC

TTACCCAGGTGAACCAGTTCACCTGATTACCCTGTTATCCCTATGCTAGCATACTT

GCTTGCCGGCATGCTTGCTAGTACCAAAACTAGCTGGTTGGCACAGGTGGGCTTGCT

TAGGCACCTGAGCAGGCAGGCTAGTACCTAAGCCAACCGGCAAGTAAGTTAGTAGG

CTCCAAAGTTCAGGTGTTGGAGTTAACTTAGGGATAACAGGGTAATAGTAGGTAG

GTTAGCTGGTTAGTAAGCTTGCCTTGGAGCTTGCTAGTTTGCTAGTTTACCAACTAAC

CGGCAAGTTAACTTTGGCACCTGTTGGTAGGCCTAAGCTTGCCAGCCCACCTGAACC

TGCCCAGGTGGGCACACCTGAGTATGCCTTGGATTACCCTGTTATCCCTAAGCACA

CCTGAGCAAGCTAGTACAGGTGCACCTGCAGGTGCCTACACCTGGGTAGGCTAACT

CACCTGTGCCTGCCTGCTGGCACACCTGAACTGGTTGGCACCTATGCCAGCTTGCCA

ACCGGCTTAGGTAGGTACCAGCCGGTATACTAGCTAACTAACCTAGGGATAACAGG

GTAATCACCTGAGTAAACCCCTAGGTAAGTACAGGTGTACCAGCTGGTTGGTTCCA

ACCTAAGCTTTGGTTGGTGCCGGCTGGTTTACCGGTATACTCCAACACCTGAGCTGG

TACCTAGGCTTACTCACCTGCAGGTGGGCTGGTACCTATGCCAACCAACCATTACCC

TGTTATCCCTACACCTGTTGGAGCTTTGGCACCTGAGCACACCTGGGCTGGCATGCT

TAGGCACCTGGGTAGGCTTAGGCAGGTGAGCAGGCTAGCTGGTAGGTTAGCCGGTA

CACCTGAGTTTACTCAGGTGCCTAAGCTGGTTTAGGAGCTGGTATAGGGGCATTGGA

GCATAGGGATAACAGGGTAATGGCTGGCAGGTTAACCAACTAACCAACTCCTAAG

CCGGTAGGCTAGCTAGCATACCTGCTAGCCCCAACACCTGTACCAGCAGGCAAGCT

GGCTCCTAAACTAGTACAGGTGAACCTGCCGGCTAGCTAGCTTAGGGGCTAGCCAGT

AGGTTATTACCCTGTTATCCCTAAGCTAGCCTGCCAGCTCCTATGCTAGTTAGCAA

GCTGGTAGGCTGGCTAGCCTGCCTACTTACCGGTTGGTAGGTAAACCCACCTGAGCA

TGCCGGTATGCCTAGGGGCTTGCCTGCCAGCCAACCTAGGTGCTGGCACCTATGCCT

ACTTAGGGATAACAGGGTAATAACTGGCTCCAACACCTGTACTAGCAAGCTTGCCA

GCAAGTATAGGCACCTGAGCTAACTAGCTTAGGAACCCACCTGGGCATAGGAACCA

GCTAGTTAGCTCCAAAGCTAACCCCTAGGTTGGTTTGCCAGCACACCTGTACTTACC

CACCTGTACTATTACCCTGTTATCCCTAAGTTAACTCCTAAGCCCACCTGTACCAA

CCAGTAGGCATTGGAGTTGGCTGGTACCTAGGCTGGCTAGCCAGCTGGTAAGCAAG

CAAGTTTACCCAGGTGGGCTCCTACAGGTGAGCTCCTAAGCTCACCTGGGTACCAAG

GCTGGCAAGCAAGCCTAGGGATAACAGGGTAATAGCTGGCTAGTTGGTAGGCTAG

CTTAGGGGCTGGCTAACCAGCAGGTAAGTAAGCACCAAAGCAGGTTGGTAAACCTT
```

-continued
GGCAGGTGAGTTGGCTAGCTTTGGAACTAGCCAGTTTACCTAGGAACTAGTTCCTAA

GCTAGTAGGTTAGTA

Figure 13:
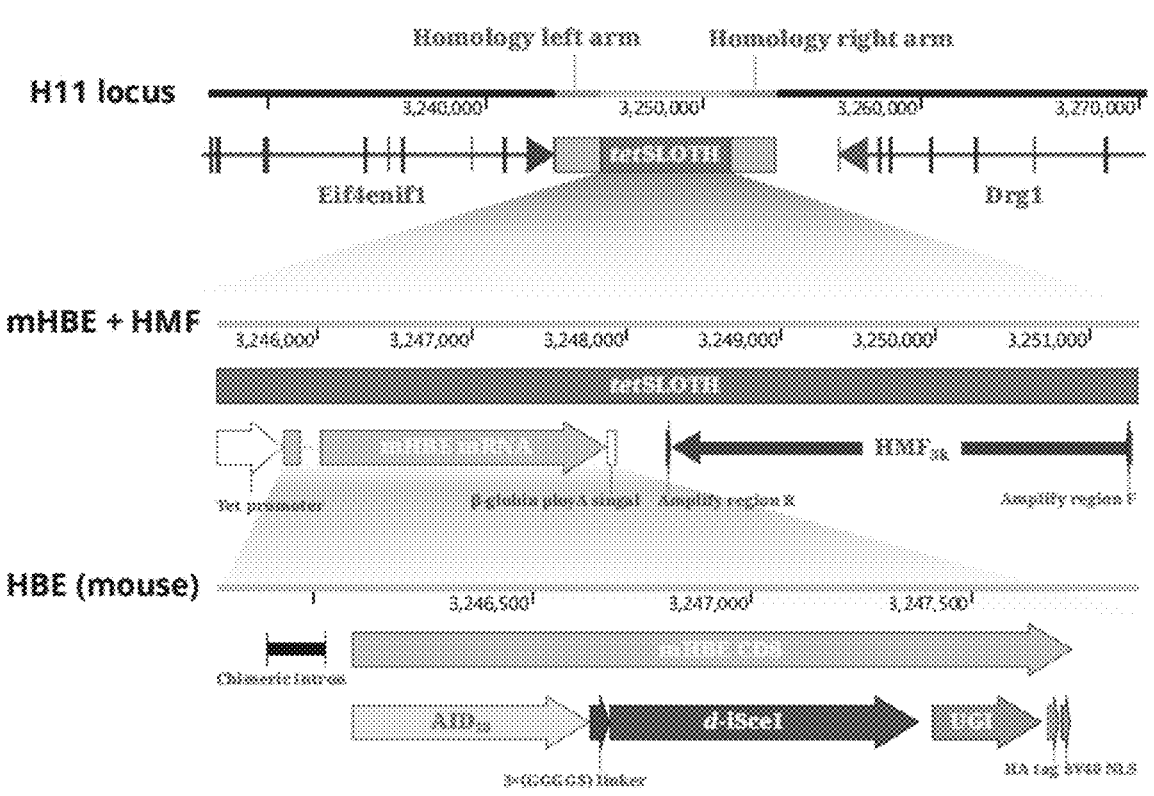
FIG. 13 is a map of the tet-SLOTH (Single-cell Lineage On Targeted Hyper-mutation) system in mice H11 transgenic locus.

Example 7 Verification of the Mutation Effect Induced by the Targeted Single-Base Editing System Constructed by the Present Application (I) Strain Construction of Tet-SLOTH Mice The mouse HBE protein (mHBE) had been codon optimized and the HA protein tag was added. The mouse HBE protein from N-terminus to C-terminus is: $AID_{10}$, 3×(GGGGS) (SEQ ID NO: 12) linker, d-I-SceI, 10aa GS rich linker, HA protein tag and SV40 nuclear localization signal, respectively. The mHBE was linked between the tet promoter and the β-globin polyA termination signal. The HMF3k tag sequence had two ends added with specific amplification sequences that can be used for specific amplification in the mouse genome, and was placed downstream of the mHBE expression frame. Together they formed the tet-SLOTH system. Using Cas9-mediated transgene technology, the tet-SLOTH system was integrated into the mouse H11 (Hipp11) locus between the Eif4enif1 and Drg1 genes. The H11 locus was located on mouse chromosome 11 and had been confirmed to be used for the stable and high-efficiency expression of exogenous genes. The transgenic locus was identified by Southern blot and confirmed to be a single copy. The map of the tet-SLOTH system in the mouse H11 transgenic locus is shown in FIG. 13.

Figure 14:
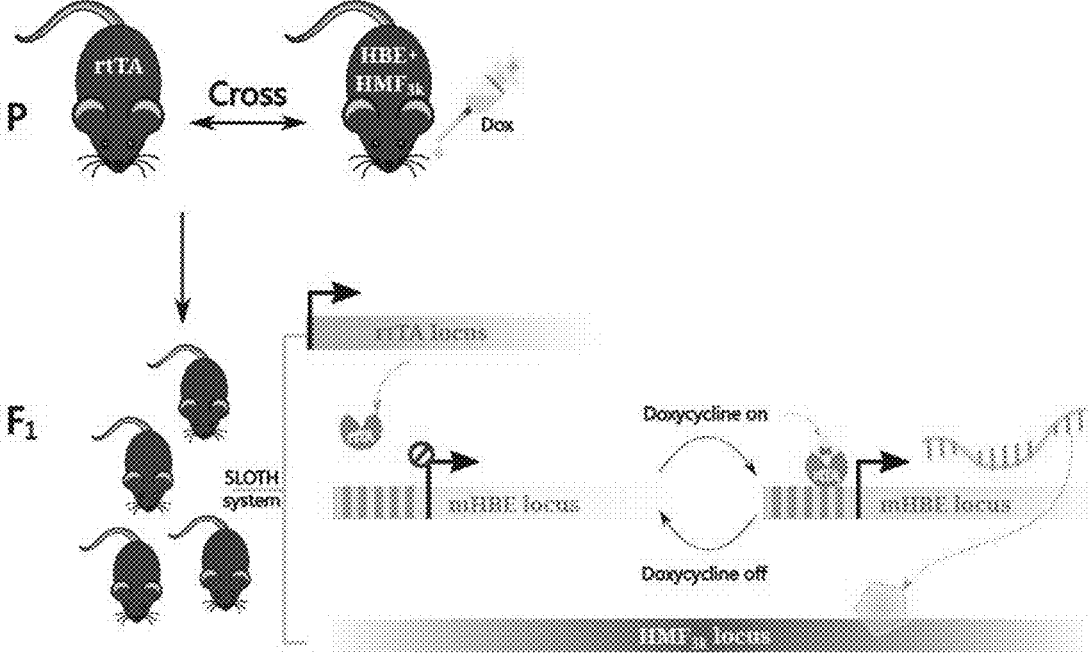
FIG. 14 is a schematic diagram of strain construction of tet-SLOTH mice.

After mating between tet-SLOTH mice and rtTA strain mice (JAX ID: 006965), in the progeny of tet-SLOTH+/rtTA+, the stably expressed rtTA protein binded to the Tet promoter upstream of HBE under the effect of doxycycline (Dox), and induced the expression of HBE protein. By controlling the intake of Dox in mice, the switch of the SLOTH system can be regulated, as shown in FIG. 14.

(II) Strain Construction of Lox-SLOTH Mice

Figure 15:
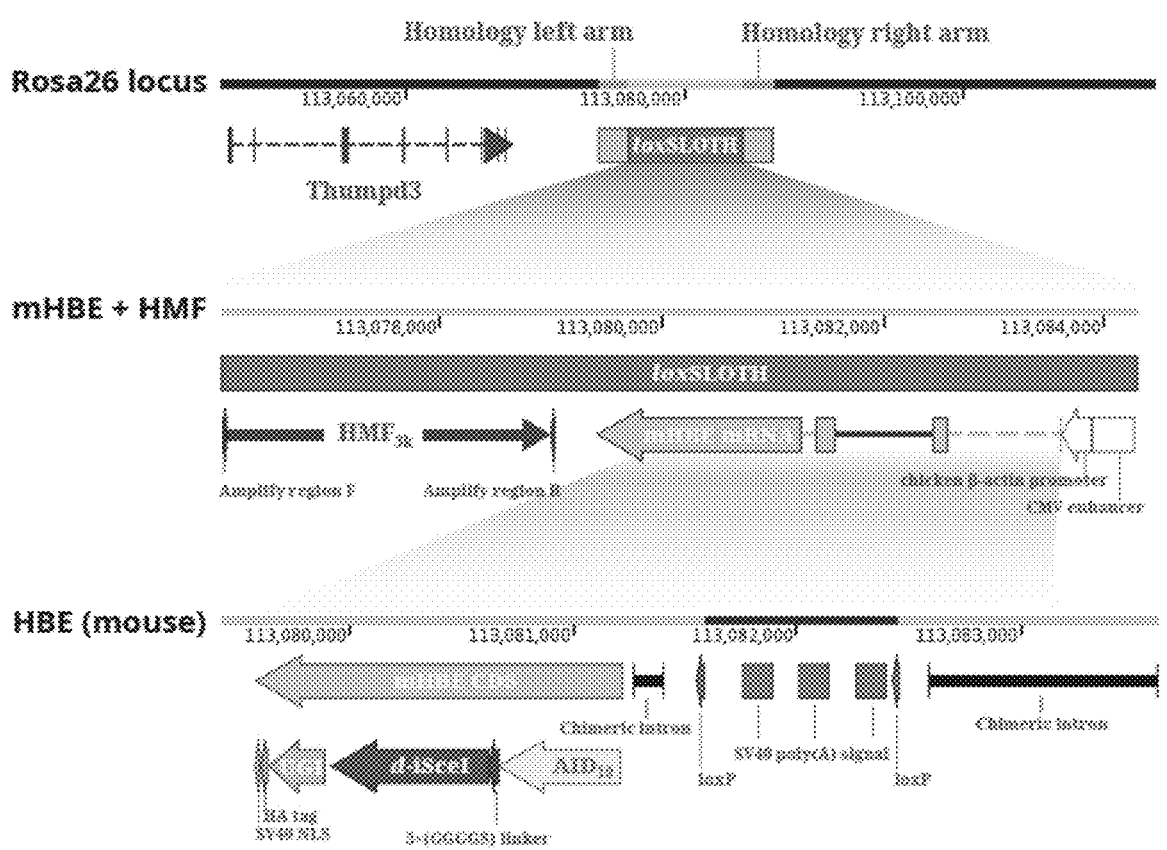
FIG. 15 is a map of the lox-SLOTH system in the mouse Rosa26 locus.
Figure 16:
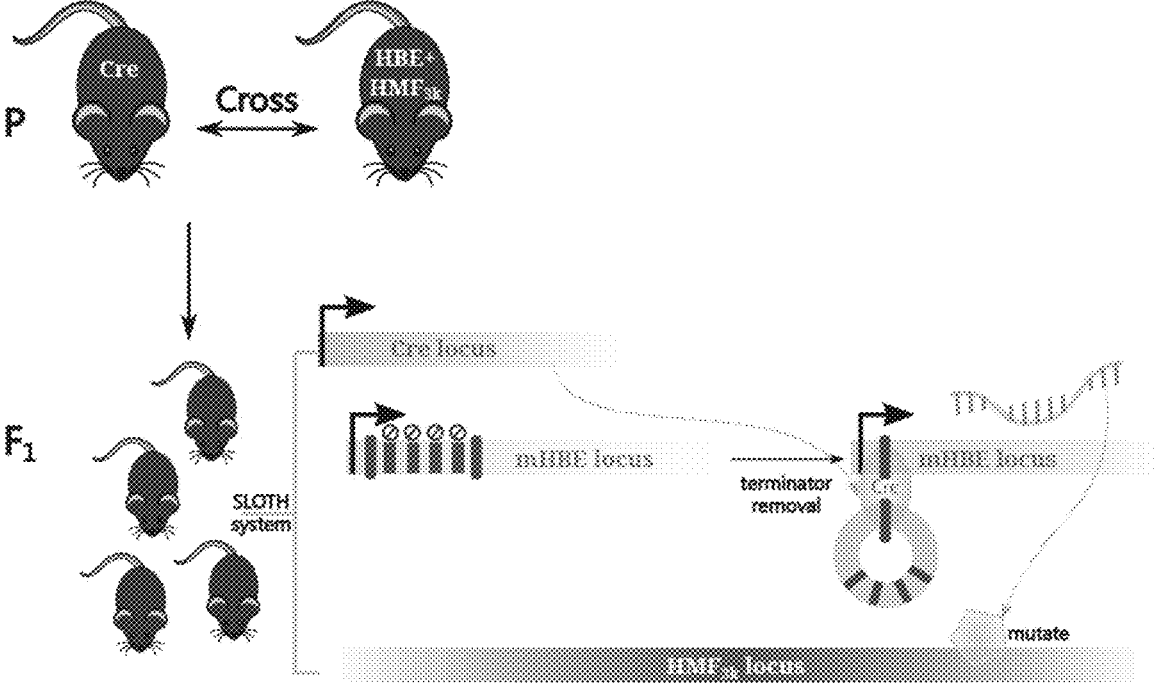
FIG. 16 is a schematic diagram of strain construction of lox-SLOTH mice.
Figure 17A:
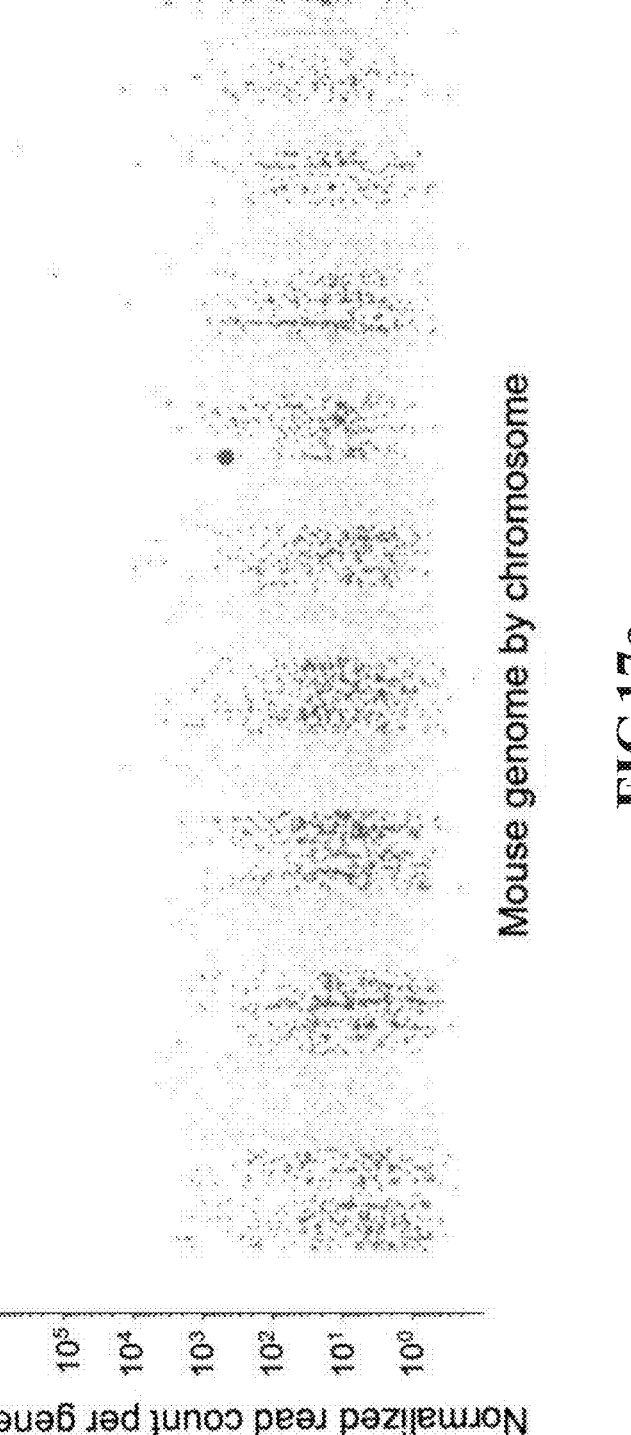
FIGS. 17a-17d are schematic diagrams of HBE gene expression in the tet-SLOTH system under Dox induction conditions. Among them.
Figure 17B:
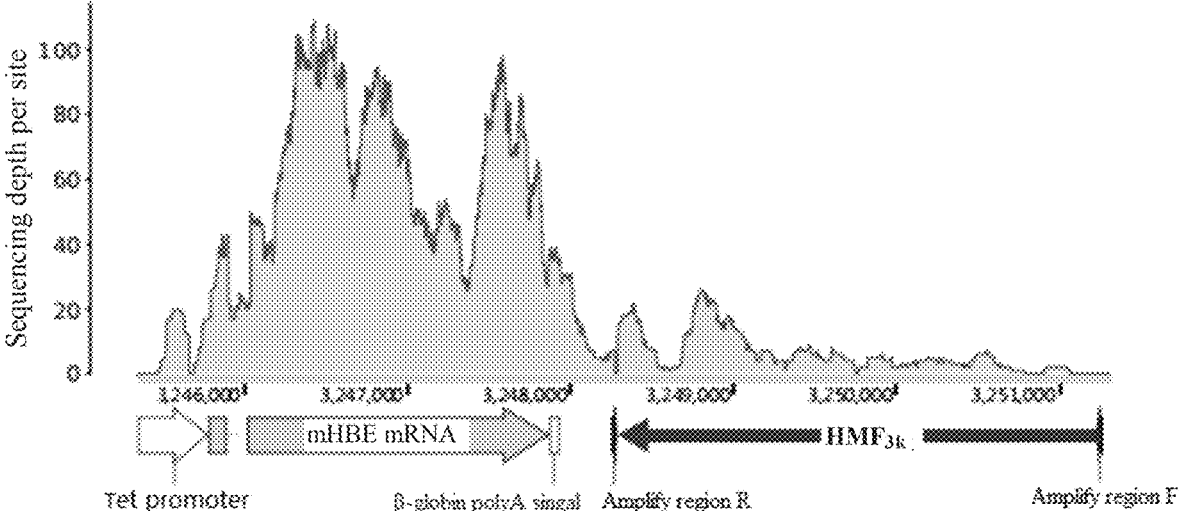
Figure 17C:
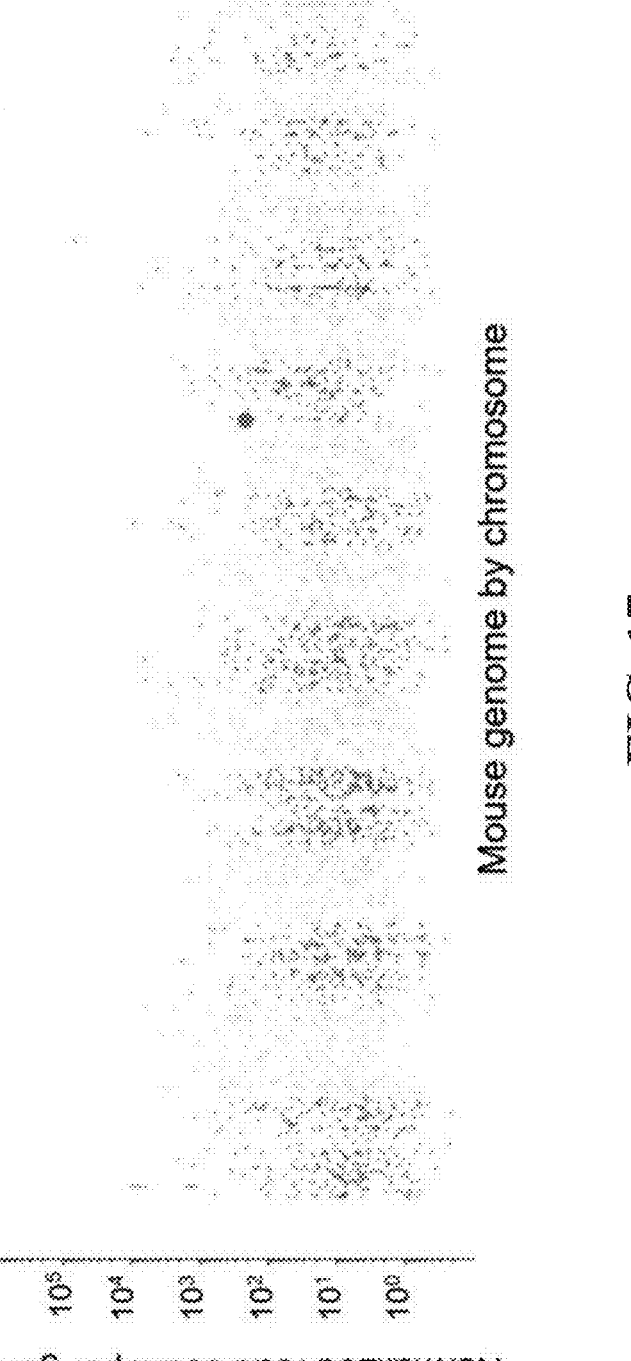
Figure 17D:
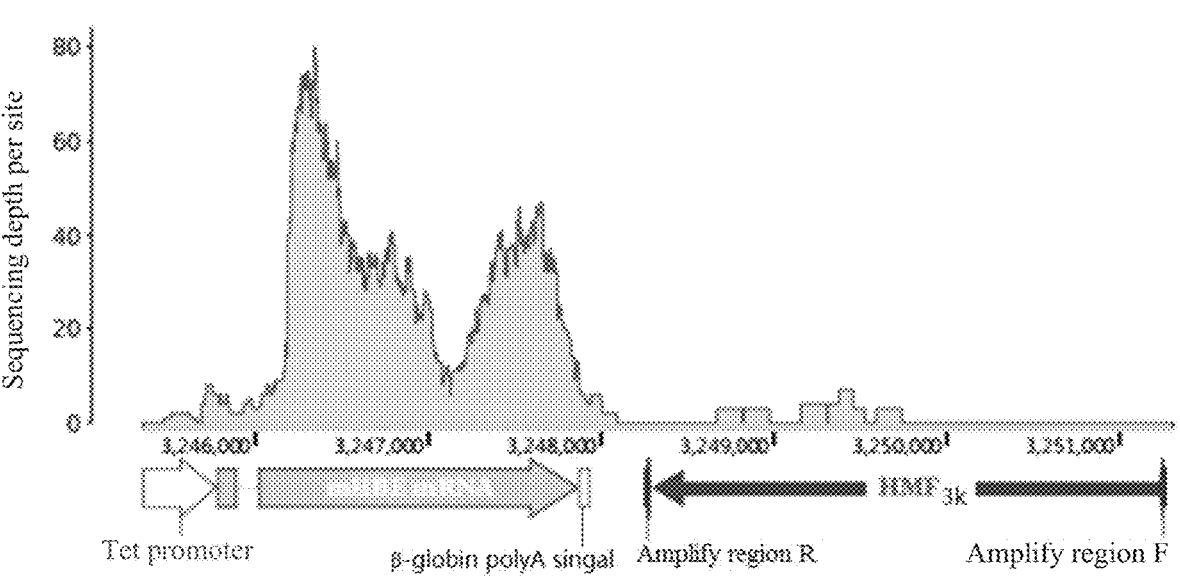

Similar to mice of the tet-SLOTH strain, the lox-SLOTH system consists of two parts: mHBE and HMF3k. The mHBE protein was connected between the chicken β-actin promoter and the polyA termination signal, and a termination signal of 3 tandem repeats with a LoxP recombination locus at both ends was inserted between the promoter and the mHBE gene. The system as a single copy was integrated into the Rosa26 locus in the mouse. The Rosa26 locus is located on mouse Chromosome 6, and is the most commonly used safe harbor for the mouse transgenic system. The foreign gene integrated into the Rosa26 locus could be stably expressed. The map of the lox-SLOTH system in the mouse Rosa26 transgenic locus is shown in FIG. 15. After lox-SLOTH mice were mated with Cre mice, in the progeny, the termination signal between the LoxP loci mediated by the Cre protein was removed, and the lox-SLOTH system was turned on, as shown in FIG. 16.

In order to verify whether the mutation inducting system can normally function in mice, a transgenic mouse strain of tet-SLOTH was selected and the following experiment was designed. Mice homozygous for the tet-SLOTH locus and mice heterozygous for rtTA were mated, and the genotypes of the progeny were tet-SLOTH+/rtTA+ and tet-SLOTH+/rtTA−. From 3 days before mating, the mother mice were fed Dox (2 mg/day) in the form of feed intake, and the fetuses could absorb Dox through the placenta to activate the expression of HBE. By comparing the survival rates and phenotype of the progeny of the two genotypes, it can be determined whether the system has an effect on the development of mice. In terms of the number of progeny (F1), there was no significant difference between tet-SLOTH+/rtTA+ and tet-SLOTH+/rtTA−, and there was no abnormality in development.

Two time points E14 and P1 were selected. After the individuals with tet-SLOTH+/rtTA+ were identified by PCR, the whole transcriptome sequencing was performed respectively. First, the hind limbs of the mouse were isolated for RNA extraction. Then 1 μg of total RNA from each sample was taken to construct a transcriptome sequencing library. Finally, the Illumina NovaSeq™ platform was used for high-throughput sequencing. The data volume of a single sample is greater than 8 Gb, and the sequencing length is PE150. The analysis steps of the sequencing data were as follows: 1) Using fastp to control the quality of the sequencing data, and filtering the sequences whose average quality is lower than Q35. 2) Using the map of the locus (FIG. 13) and its sequence, on the basis of the mouse reference genome (Mus musculus, GRCm38), and creating an index and annotation file for sequence alignment. 3) Comparing RNAseq data through STAR. 4) Calculating the effective sequencing read and gene length (subread/featureCount) of each gene. As shown in FIGS. 17a-17d, at different developmental time points, Dox can induce the expression of HBE gene in tet-SLOTH transgenic mice. The expression level of HBE is relatively high, and it has stable expression level during mouse development. This means that, unlike previous work, the labeling efficiency of the SLOTH system is constant and can better restore the time points of the cell development history.

Figure 18A:
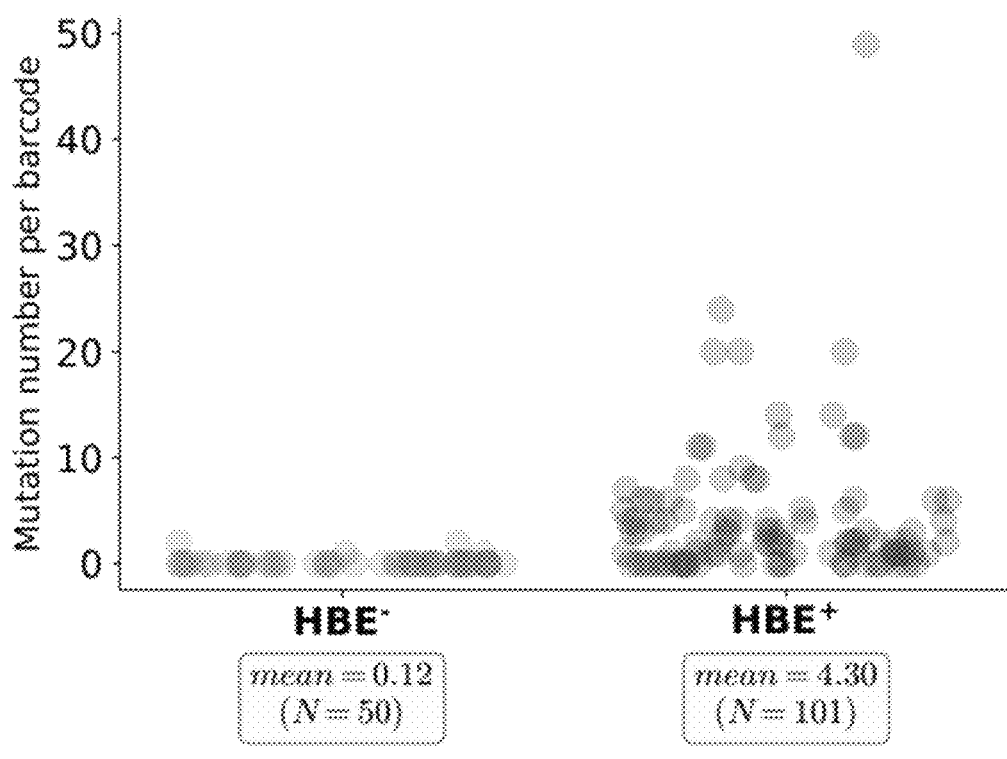
FIGS. 18a-18c are statistical graphs of the number of mutation events on the HMF3k fragment in the mouse system. Among them.
Figure 18B:
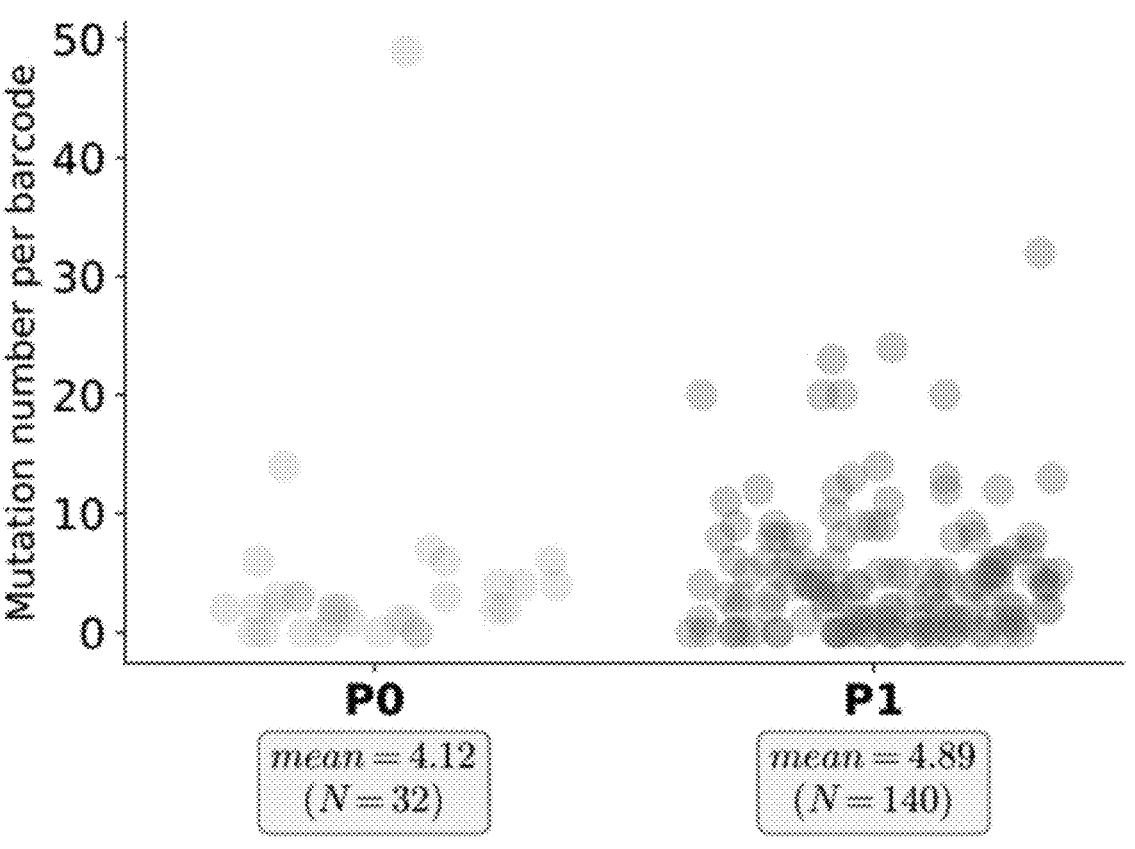
Figure 18C:
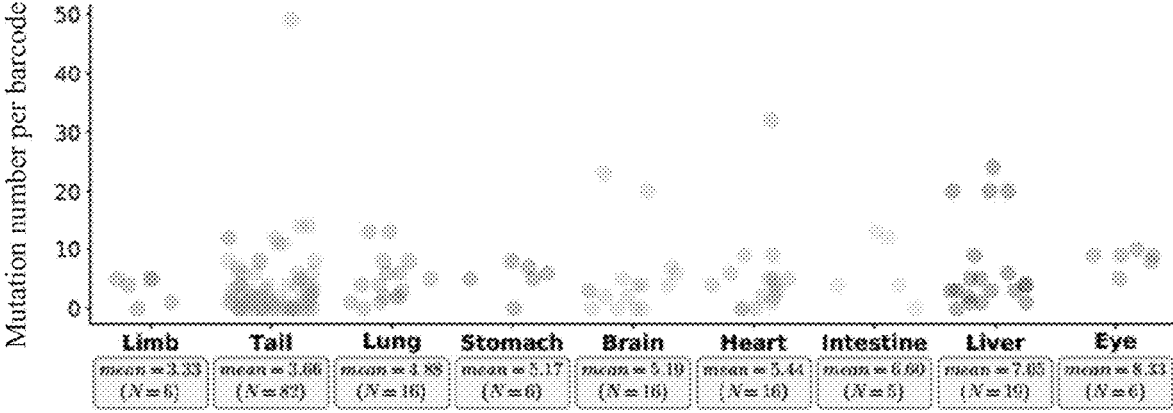

In order to compare the mutations on a single molecule of HMF3k, different organ types in each individual mouse were amplified, monoclonalized with TOPO™ cloning kit, and single clones were randomly selected for Sanger sequencing. It can be seen from FIGS. 18a-18c that in the HBE⁻ control group, almost no mutations were observed in the HMF3k labeling sequence; while in the HBE⁺ experimental group, there were 4.3 mutations on average per unit labeling sequence. It is proved that the system can function normally in mice and successfully induce mutations.

The above-mentioned embodiments only convey several embodiments of the present application, and the descriptions are more specific and detailed, but they should not be understood as limiting the scope of the present application. It should be pointed out that for those of ordinary skill in the art, without departing from the concept of the present application, several modifications and improvements can be made, and these all fall within the protection scope of the present application. Therefore, the protection scope of the present application should be subject to the appended claims.

The sequences involved in this application include the following:

The nucleotide sequence encoding the HBE protein applicable to zebrafishes and mouse:

(SEQ ID NO: 5, 1638 nucleotides)
ATGGACAGCCTCCTTATGAACCGGCGAGAGTTCTTGTATCAATTTAAAAA

CGTTCGATGGGCAAAGGGACGGCGGGAGACTTACCTTTGCTATGTTGTGG

-continued

AGCGGCGAGATTGCGCCACCTCTTTCTCTCTTGACTTCGGCTATCTCCGA

AACAAGAATGGATGTCACGTAGAACTTTTGTTTCTTCGGTATATAAGTGA

CTGGGACCTTGATCCAGGACGATGCTACCGCGTTACCTGGTTCATCTCAT

GGAGCCCCTGTTATGACTGCGCCAGGCATGTTGCTGACTTTCTGAGAGGG

AATCCAAACCTCTCCCTCCGCATTTTCGCTGCTAGGCTGTATTTTTGTGA

GGATCGGAAGGCAGAACCAGAGGGTCTCAGGCGATTGCGCCGGGCTGGAG

TACAAATCGCTATTATGACATTTAAGGACTACTTTTATTGCTGGAACACT

TTCGCTGAAAATCATGGTAGAACCTTTAAAGCCTGGGAGGGGCTTCACGA

GAACTCAGTCCGATTGTCAGGTCAACTCAGGCGCATACTGGGAGGAGGTG

GTTCCGGCGGTGGGGGCAGTGGCGGAGGTGGTTCTATGAAGAATATCAAG

AAAAATCAGGTAATGAATTTGGGTCCTAACAGTAAGTTGCTCAAGGAATA

CAAGTCCCAACTGATTGAGCTGAACATTGAACAATTCGAAGCCGGAATTG

GCTTGATACTCGGCAATGCTTATATCAGGAGTAGAGATGAAGGGAAAACT

TATTGCATGCAATTCGAGTGGAAAAATAAGGCCTATATGGATCACGTGTG

TCTCCTTTATGACCAATGGGTACTGTCACCTCCACATAAGAAAGAGAGGG

TTAATCATCTTGGTAATCTCGTTATCACATGGGGAGCACAAACTTTCAAA

CATCAGGCATTTAACAAATTGGCAAACTTGTTTATTGTGAACAATAAAAA

GACTATACCCAACAATTTGGTCGAGAACTATCTTACCCCTATGTCTTTGG

CCTACTGGTTCATGGACGCAGGCGGCAAATGGGATTACAACAAAAATAGT

ACAAACAAAGTATTGTACTTAACACACAGTCCTTTACATTCGAAGAGGT

AGAATATTTGGTCAAAGGACTTAGGAACAAGTTTCAACTGAATTGTTACG

TTAAAATAAATAAAAATAAGCCTATCATATACATAGACTCTATGTCTTAC

-continued

CTGATTTTCTACAACTTGATAAAGCCCTACCTCATTCCCCAAATGATGTA

TAAACTCCCAAATACTATTTCTTCCGAGACCTTCCTGAAAtctggtggtt ctggaggatctggtggttctactaatctgtcagatattattgaaaaggag accggtaagcaactggttatccaggaatccatcctcatgctcccagagga ggtggaagaagtcattgggaacaagccggaaagcgatatactcgtgcaca ccgcctacgacgagagcaccgacgagaatgtcatgcttctgactagcgac gcccctgaatacaagccttgggctctggtcatacaggatagcaacggtga gaacaagattaagatgctctctggtggttcttacccatacgatgttccag attacgctgcagctcccaagaagaagaggaaagtctaa The amino acid sequence of the HBE protein applicable to zebrafishes and mouse:
   (SEQ ID NO: 13, 545 amino acid residues)
MDSLLMNRREFLYQFKNVRWAKGRRETYLCYVVERRDCATSFSLDFGYLR

NKNGCHVELLFLRYISDWDLDPGRCYRVTWFISWSPCYDCARHVADFLRG

NPNLSLRIFAARLYFCEDRKAEPEGLRRLRRAGVQIAIMTFKDYFYCWNT

FAENHGRTFKAWEGLHENSVRLSGQLRRILGGGSGGGGSGGGGSMKNIK

KNQVMNLGPNSKLLKEYKSQLIELNIEQFEAGIGLILGNAYIRSRDEGKT

YCMQFEWKNKAYMDHVCLLYDQWVLSPPHKKERVNHLGNLVITWGAQTFK

HQAFNKLANLFIVNNKKTIPNNLVENYLTPMSLAYWFMDAGGKWDYNKNS

TNKSIVLNTQSFTFEEVEYLVKGLRNKFQLNCYVKINKNKPIIYIDSMSY

LIFYNLIKPYLIPQMMYKLPNTISSETFLKSGGSGGSGGSTNLSDIIEKE

TGKQLVIQESILMLPEEVEEVIGNKPESDILVHTAYDESTDENVMLLTSD

APEYKPWALVIQDSNGENKIKMLSGGSYPYDVPDYAAAPKKKRKV*

---

The invention claimed is:

1. A targeted single-base editing protein, comprising the amino acid sequence that is encoded by the nucleotide sequence of SEQ ID NO: 5.

2. A targeted single-base editing system, comprising the targeted single-base editing protein according to claim 1 and a target hyper mutation sequence.

3. The targeted single-base editing system according to claim 2, wherein the target hyper mutation sequence comprises the nucleotide sequences set forth in SEQ ID NO; 6 and SEQ ID NO: 7.

* * * * *